(12) United States Patent
Godfrey, Jr. et al.

(10) Patent No.: US 8,758,213 B1
(45) Date of Patent: Jun. 24, 2014

(54) MINIMALLY INVASIVE APPLICATORS FOR ROBOTIC AND NON-ROBOTIC-ASSISTED INTRAOPERATIVE RADIOTHERAPY

(76) Inventors: Loren Godfrey, Jr., Kinnelon, NJ (US); Loren Godfrey, Sr., Farmington, CT (US)

( * ) Notice: Subject to any disclaimer, the term of this patent is extended or adjusted under 35 U.S.C. 154(b) by 1337 days.

(21) Appl. No.: 12/416,677

(22) Filed: Apr. 1, 2009

Related U.S. Application Data

(60) Provisional application No. 61/098,408, filed on Sep. 19, 2008.

(51) Int. Cl.
*A61N 5/00* (2006.01)

(52) U.S. Cl.
USPC .................................. 600/3; 600/7; 604/116

(58) Field of Classification Search
USPC .................... 600/1–8; 604/116, 117; 606/130
See application file for complete search history.

(56) References Cited

U.S. PATENT DOCUMENTS

| | | | | |
|---|---|---|---|---|
| 3,060,924 A | * | 10/1962 | Rush | 600/6 |
| 4,331,131 A | * | 5/1982 | Kumar | 600/6 |
| 7,022,062 B1 | * | 4/2006 | Murphy | 600/7 |

* cited by examiner

*Primary Examiner* — Charles A Marmor, II
*Assistant Examiner* — Carrie R Dorna
(74) *Attorney, Agent, or Firm* — Michael D. Eisenberg

(57) ABSTRACT

An applicator is provided, for manipulating one or more catheters carrying a radiation generating device, for delivering a radiation field to a target, the applicator having a proximal end and a distal end. The applicator includes: a spring mechanism; at least one catheter grasper for grasping one or more catheters carrying a radiation generating material, the catheter grasper being attached to the spring mechanism; and a sheath, for covering at least a portion the spring mechanism. The spring mechanism is designed for being retracted within the sheath, in a closed configuration of the applicator. The spring mechanism is designed for being released into a predetermined arrangement when moved out of a distal end of the sheath, in an open configuration of the applicator. The applicator is designed to be repeatedly switched between the closed configuration and the open configuration.

13 Claims, 15 Drawing Sheets

MINIMALLY INVASIVE APPLICATORS FOR ROBOTIC AND NON-ROBOTIC-ASSISTED INTRAOPERATIVE RADIOTHERAPY

CROSS-REFERENCES TO RELATED APPLICATIONS

This application claims priority from U.S. application Ser. No. 61/098,408 filed Sep. 19, 2008, which is hereby incorporated herein by reference in its entirety.

TECHNICAL FIELD

The present invention relates to minimally invasive applicators for robotic-assisted and non-robotic assisted intraoperative radiotherapy.

BACKGROUND OF THE INVENTION

Radiation therapy has a long history of providing increased local and regional control of disease when used after surgery for malignancies of the brain, head & neck, lung, breast, stomach, pancreas, colon, rectum, uterus, cervix, prostate, skin, esophagus, kidney, bladder, ovary and soft tissues (sarcomas). Traditionally, the majority of radiotherapy was delivered via an external radiation source, called external beam radiotherapy or EBRT. About 90% of radiotherapy is given via EBRT. The remainder is given via techniques where a radioactive isotope is placed within close proximity to a targeted tumor, called brachytherapy.

Intraoperative radiotherapy (IORT) is a subspecialty in which the radiotherapy is given at the time of surgery. Its primary advantage is the ability to surgically remove organs-at-risk from the post-operative field during treatment, enabling higher doses to be given safely. IORT has been in use for many years at specialized facilities and has a wealth of clinical data to support its safety and efficacy. Both EBRT and brachytherapy protocols have been developed for IORT. A disadvantage of IORT is the tremendous capital costs associated with setting up a program, since a fully-equipped operating room (OR) and a shielded radiotherapy delivery room must be functionally united. This has limited the expertise to select centers.

Two concomitant developments have created an opportunity to overcome the current limitations of IORT. One is the development of electronic brachytherapy. A catheter-based radiotherapy system that produces ionizing radiotherapy from a very small source. It can effectively reproduce radiotherapy fields that were generated with seed-sized isotopes. Its treatment energy is low enough that expensive shielding is not required, and as it is not radioactive (when the machine is off), expensive procedures and protections are not required. This has just recently been FDA approved in for treatment of breast and skin cancers and has not been used intraoperatively yet as of the time of the filing of this document.

The second development is surgical robotics. A success story developing over the previous decade, surgical robots have facilitated more and more minimally invasive procedures, including oncologic resections. The rapid recovery time and shortened hospital stays have been well-received in all applications. Prostatectomies and hysterectomies comprise the majority of oncologic surgeries, though this is evolving. Patients are evaluated for post-operative radiotherapy in the same manner after either a robotic or traditional resection.

Combining the two technologies in the IORT setting would realize several practical advantages. Electronic brachytherapy does not require significant capital costs. It can be applied in ORs in use today. And the robotics would maintain the minimally invasive surgical advantage. This is clearly of interest to many.

The manner in which the systems can be integrated, however, is not particularly clear. Delivering radiotherapy at the time of resection requires precise calculations to be done in "real time" and these systems do not exist for electronic brachytherapy. Currently, balloon applicators are used, primarily because the dosimetry is simple. Balloon applicators, however, do not facilitate customization of the radiotherapy fields. It is possible that other traditional applicators can be used, though none of these would enable minimally invasive surgery, real-time dosimetry, and customization of the radiotherapy fields.

Therefore there is a need for a set of applicators that would satisfy both requirements, namely, be minimally invasive and permit real-time dosimetry, as well as customization of the radiotherapy fields. It is also contemplated, that the present invention can be used in non-robotic environments and achieve advantages over previous devices.

BRIEF SUMMARY OF EMBODIMENTS OF THE INVENTION

The present invention, in some embodiments thereof, relates to an applicator for manipulating one or more catheters carrying a radiation generating device, for delivering a radiation field to a target, the applicator being characterized by a spring mechanism, which settles into a predetermined arrangement, when moved out of a sheath, designed for covering the spring mechanism.

An aspect of some embodiments of the present invention relates to an applicator for manipulating one or more catheters carrying a radiation generating device, for delivering a radiation field to a target, the applicator having a proximal end and a distal end. The applicator includes: a spring mechanism; at least one catheter grasper for grasping one or more catheters carrying a radiation generating material, the catheter grasper being attached to the spring mechanism; and a sheath, for covering at least a portion the spring mechanism. The spring mechanism is designed for being retracted within the sheath, in a closed configuration of the applicator. The spring mechanism is designed for being released into a predetermined arrangement when moved out of a distal end of the sheath, in an open configuration of the applicator. The applicator is designed to be repeatedly switched between the closed configuration and the open configuration.

Optionally, the spring mechanism is designed for being attached to a plurality of catheter graspers.

In a variant, the above applicator is designed for delivering one of a plurality of predetermined radiation fields to the target. The catheter grasper is designed for holding the catheter at any of a plurality of predetermined positions along the catheter, each position corresponding to one of the plurality of predetermined radiation fields.

In another variant, the above applicator is designed for delivering one of a plurality of predetermined radiation fields to the target. The spring mechanism is designed for assuming a plurality of predetermined arrangements in the open configuration, each arrangement corresponding to one of the plurality of the predetermined radiation fields.

In a further variant, the spring mechanism includes one wire spring bent about itself.

In yet a further variant, the wire spring is designed for being released and assuming a curved shape, when moved out of the sheath, in the open configuration of the applicator.

According to some embodiments of the present invention, the spring mechanism comprises a plurality of wire springs, each wire spring being attached to at least one catheter grasper.

Optionally, proximal sections of the wire springs are joined together into a wire mesh, such that the wire springs are designed for being moved together along a direction of a central axis of the sheath.

According to other embodiments of the present invention, the above applicator is designed for holding a plurality of catheters, wherein the wire springs are designed to be released into the plurality of arrangements, each arrangement being characterized by a distance between at least two specific graspers, the distance between the graspers increasing as the wire springs are moved out of the distal end of the sheath, and decreasing, as the wire springs are retracted into the sheath.

In a variant, the above applicator further comprises an anchor, for keeping a distance between the wire springs fixed at an anchoring location along the wire springs, the anchor being attached to the wire springs and moving with the wire springs along the direction of the central axis the sheath. The wire springs are fastened together at some locations proximal of the anchor, and are separated at locations distal of the anchor.

In another variant, the wire mesh comprises a proximal wire mesh section and a distal wire mesh section, the sections being separated by a hinging mechanism, such that the hinging mechanism is designed for being controllably rotated, thereby rotating the distal wire mesh section together with the wire springs and the graspers, with respect to the proximal wire mesh section.

In a further variant, the catheter graspers are set in line according to each other, so that each catheter grasper is designed to grasp a different section of a single catheter.

In yet a further variant, the applicator further includes at least one straight wire for holding at least one further catheter grasper. The straight wire is designed for being moved with the plurality of wire springs, and does not form a curved shape when moved out of the distal end of the sheath.

Another aspect of some embodiments of the present invention relates to a device for aiming a radiation field toward a target area, the device having a proximal end and a distal end. The device includes: a spring mechanism; a film having markings forming a grid, the film being held by the spring mechanism, and being designed for being applied to the target area, thereby defining sub-areas on the target area, the sub-areas being delineated by a shape of the grid; a sheath, for covering at least a portion the spring mechanism. The spring mechanism is designed for being retracted within the sheath, in a closed configuration of the applicator. The spring mechanism is designed for being released into a predetermined arrangement when moved out of a distal end of the sheath, such that the film is stretched, in an open configuration of the applicator. The device is designed for being repeatedly switched between the closed configuration and the open configuration.

Optionally, the spring mechanism comprises a left wire spring and a right wire spring, the film being attached to the left wire spring and the right wire spring, and the left and right wire springs being designed for being released into a curved shape when moved out of a distal end of the sheath.

In a variant, the above device further includes a straight wire. The straight wire does not form a curved shape, when moved out of the sheath. The straight wire is between the left and right wire springs. The straight wire is attached to the film. The straight wire is designed to be controllably rotated about a central axis thereof, thereby rotating the stretched film around the central axis of the middle wire.

According to some embodiments of the present invention, a method is provided for delivering radiation to a target area. The method includes: mapping a plurality of radiation fields; inserting the above aiming device of in the closed configuration thereof into a cavity, though an incision; switching to an open configuration of the device inside the cavity; applying the film onto the target area, thereby dividing the target area into sub-areas defined by the grid; inserting a catheter carrying a radiation generating material into the cavity; moving the catheter over a desired sub-area; and delivering radiation to the desired sub-area for a predetermined length of time.

In a variant, the above method further includes after the switching, at least one of the following: rotating the film about a central axis of the sheath; and rotating the film about an axis not parallel to the central axis of the sheath.

In another variant, the above method further includes: moving the catheter sequentially over a plurality of sub-areas; and delivering radiation to each of sub-areas for a preset length of time. The total radiation delivered to the target area is one of the plurality of mapped radiation fields.

Another aspect of some embodiments of the present invention relates to a method for delivering a radiation field to a target through an applicator. The method includes: mapping a plurality of radiation fields according to a plurality of arrangements of the applicator; selecting a radiation field to be delivered among the plurality of radiation fields; inserting the applicator in a closed configuration into a cavity, though an incision; switching to an open configuration of the applicator inside the cavity; inserting at least one catheter carrying a radiation generating material into the cavity; grasping the at least one catheter with at least one grasper of the applicator at a predetermined position along the catheter; setting the applicator and the at least one catheter according to an arrangement corresponding the selected radiation field; and delivering the selected radiation field to the target.

Optionally, the setting includes at least one of the following: inserting a selected number of catheters into one or more graspers; moving at least one catheter along one grasper to a selected distance from the target; setting at least two graspers at one of a plurality of predetermined distances from each other; and rotating the graspers about at least one axis.

Other features and aspects of the invention will become apparent from the following detailed description, taken in conjunction with the accompanying drawings, which illustrate, by way of example, the features in accordance with embodiments of the invention. The summary is not intended to limit the scope of the invention, which is defined solely by the claims attached hereto.

Implementation of the method and/or system of embodiments of the invention can involve performing or completing selected tasks manually, automatically, or a combination thereof. Moreover, according to actual instrumentation and equipment of embodiments of the method and/or system of the invention, several selected tasks could be implemented by hardware, by software or by firmware or by a combination thereof using an operating system.

For example, hardware for performing selected tasks according to embodiments of the invention could be implemented as a chip or a circuit. As software, selected tasks according to embodiments of the invention could be implemented as a plurality of software instructions being executed by a computer using any suitable operating system. In an exemplary embodiment of the invention, one or more tasks according to exemplary embodiments of method and/or system as described herein are performed by a data processor, such as a computing platform for executing a plurality of instructions. Optionally, the data processor includes a volatile memory for storing instructions and/or data and/or a non-volatile storage, for example, a magnetic hard-disk and/or removable media, for storing instructions and/or data. Optionally, a network connection is provided as well. A display and/or a user input device such as a keyboard or mouse are optionally provided as well.

BRIEF DESCRIPTION OF THE DRAWINGS

The present invention, in accordance with one or more various embodiments, is described in detail with reference to the following figures. The drawings are provided for purposes of illustration only and merely depict typical or example embodiments of the invention. These drawings are provided to facilitate the reader's understanding of the invention and shall not be considered limiting of the breadth, scope, or applicability of the invention. It should be noted that for clarity and ease of illustration these drawings are not necessarily made to scale.

Some of the figures included herein illustrate various embodiments of the invention from different viewing angles. Although the accompanying descriptive text may refer to such views as "top," "bottom" or "side" views, such references are merely descriptive and do not imply or require that the invention be implemented or used in a particular spatial orientation unless explicitly stated otherwise.

Figure 1:
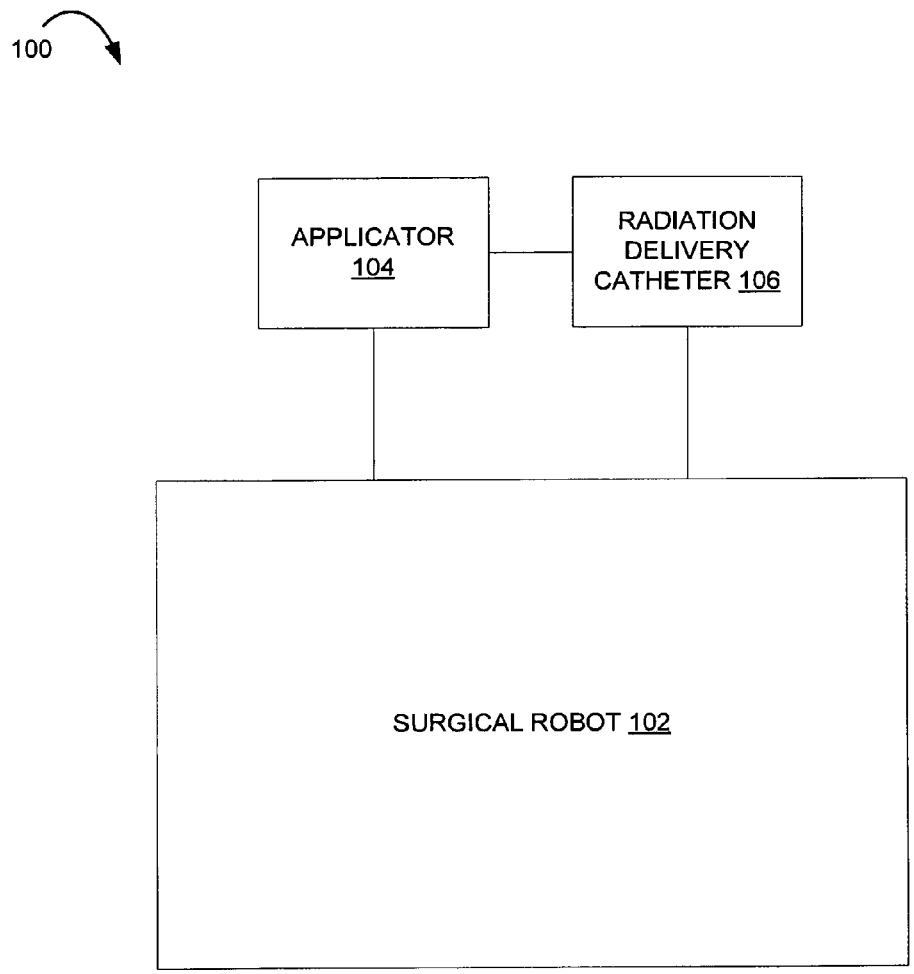
FIG. 1 is a schematic diagram illustrating a system for delivering radiation to a target, according to some embodiments of the present invention.

The figures are not intended to be exhaustive or to limit the invention to the precise form disclosed. It should be understood that the invention can be practiced with modification and alteration, and that the invention be limited only by the claims and the equivalents thereof.

DETAILED DESCRIPTION OF THE EMBODIMENTS OF THE INVENTION

From time-to-time, the present invention is described herein in terms of example environments. Description in terms of these environments is provided to allow the various features and embodiments of the invention to be portrayed in the context of an exemplary application. After reading this description, it will become apparent to one of ordinary skill in the art how the invention can be implemented in different and alternative environments.

Unless defined otherwise, all technical and scientific terms used herein have the same meaning as is commonly understood by one of ordinary skill in the art to which this invention belongs. All patents, applications, published applications and other publications referred to herein are incorporated by reference in their entirety. If a definition set forth in this section is contrary to or otherwise inconsistent with a definition set forth in applications, published applications and other publications that are herein incorporated by reference, the definition set forth in this document prevails over the definition that is incorporated herein by reference.

Before describing aspects and embodiments of the present invention, some term are to be defined. In this document, the term "proximal", when referred to a section of an object, refers to the section of the object which is farther from the target and closer to the device which holds and/or controls the object. Consequently, the term "distal" refers to a section of the object which is closer to the target and farther from the device which holds and/or controls the object. An "inner surface" refers to a surface, which faces the center of the object referred to. An "outer surface" refers to a surface which faces away from the center of the object and towards the environment in which the object is contained.

The present invention relates to minimally invasive applicators for robotic-assisted and non-robotic assisted intraoperative radiotherapy.

An aspect of some embodiments the present invention relates to an applicator for manipulating one or more catheters carrying a radiation generating device, for delivering a radiation field to a target. The applicator includes a sheath, a spring mechanism at least partially housed in the sheath, and a catheter grasper, attached to a distal section of the spring mechanism and designed for grasping and holding the catheter. The spring mechanism is controlled by a user, for example directly or through an arm of a surgical robot, and is designed for being moved in and out of the sheath, through an opening at a distal end of the sheath. When the spring mechanism moves out of the distal end of the sheath, the applicator is defined to be in an open configuration, and the spring mechanism is released into a predetermined arrangement.

The arrangement of the spring influences the location of the grasper with respect to the target. Once the position of the grasper is fixed, the grasper is designed to hold the catheter at a specific position along the catheter. The radiation field delivered to the target by the catheter depends upon the arrangement of the spring mechanism and the position at which the catheter is held out of any of a plurality of positions along the catheter. This radiation field is generally mapped before radiation treatment, so that a known radiation field is delivered to the target.

According to some embodiments of the present invention, the grasper may grasp the catheter at a plurality of different positions along the catheter. At each of such positions, the radiation delivery material is at a different distance from the target, and therefore a plurality of radiation fields may be delivered to the target, through the use of the applicator. These plurality of radiation fields may also be mapped before the treatment, so that a desired radiation field may be delivered to the target during the treatment.

Optionally, the spring mechanism may assume a plurality of arrangements, in the open configuration of the applicator. In each arrangement, the distance between the grasper and the target is different, and therefore at least one different radiation field corresponds each arrangement.

In a preferred embodiment of the present invention, the spring mechanism of the applicator includes a plurality of spring wires, and each spring wire holds at a distal end thereof a grasper, which may hold a plurality of catheters. Such an applicator allows for a plurality of radiation fields. The desired radiation field may be chosen from the plurality of radiation fields and applied to the target, according to at least one property of the target, such as shape or composition, for example.

Another aspect of some embodiments of the present invention relates to a device for aiming a radiation field toward a target area. The device is characterized by a film, optionally transparent, having markings which form a grid. The film is designed to be applied over a target area, and therefore defines sub-areas on the target area, the sub-areas being delineated by the shape of the grid. A selected radiation field is applied to the target by moving a delivery catheter into proximity with selected sub areas, and irradiating the selected areas for specific lengths of time. The film is held by a spring mechanism, which may be repeatedly moved into and out of a sheath through a distal end of the sheath. The spring mechanism is controlled by a user, for example through an arm of a surgical robot. When the spring mechanism is moved out of a distal end of the sheath, the spring mechanism is released into an arrangement, such that the film is stretched. Once the film is stretched, the film may be applied to the target area.

The above device may be used in conjunction with a radiation delivery catheter controlled by a user, for example through a surgical robot. Once the film is applied to the target area, the catheter is moved to deliver a desired amount of radiation to selected sub-areas. In this manner, a desired radiation field is applied to the target area, the radiation field being chosen according to at least one property of the target.

Referring now to the figures, FIG. 1 is a schematic diagram illustrating a system for 100 delivering radiation to a target, according to some embodiments of the present invention.

The system 100 includes a surgical robot 102, an applicator 104, and a radiation delivery catheter 106. The surgical robot 102 has at least one arm. At first, the arm is designed for holding and moving the applicator 104. After the applicator 104 is brought to a position selected by the user, the applicator is externally secured to the selected position, and the arm of the surgical robot 102 is disconnected from the arm and is used for manipulating—for holding and moving—the catheter 106. In an exemplary embodiment of the present invention, the applicator 104 is secured by an immobilized mechanical arm attached directly to an operating table upon which a patient is located—therefore maintaining the applicator 104 in a fixed position relative to the patient. The applicator 104 is inserted into a cavity near the target that is to be treated through a port or incision, and moved to a location in the proximity of the target. Once the desired location is reached by the applicator 104, the applicator 104 is set to an open configuration, a grasper of the applicator is set at a predetermined distance from the target and is ready to receive the catheter 106. The catheter 106 is introduced into the cavity, either through the same port as the applicator 104, or through a different port. The catheter 106 is moved so that the grasper of the applicator 104 grasps the catheter 106 at a desired position along the catheter 106. The radiation is then delivered, according to a predetermined dosage.

The target may be, for example, a malignancy of the brain, head & neck, lung, esophagus, breast, stomach, pancreas, colon, rectum, uterus, cervix, prostate, skin, esophagus, kidney, bladder, ovary and soft tissues (sarcoma).

Optionally, the applicator 104 includes a plurality of graspers, and therefore may hold a plurality of catheters. In such a case, a plurality of catheters are delivered one by one to graspers located near specific locations on a target area, and each catheter delivers a desired dosage of radiation to the specific location. Such a setting allows the delivery of many localized radiation fields on a target area. Furthermore, in such a setting, only specific locations on the target area in need of treatment are exposed to radiation, rather than a whole target area.

In surgery, surgical robots are generally designed to be slaves of the user. Therefore, in this document, it is understood that the surgical robot 102 is a slave of the user, and cannot act independently of the user. The surgical robot 102 may be any surgical robot known in the art. In an exemplary embodiment, the surgical robot 102 is manufactured by Intuitive Surgicals. In a preferred embodiment of the present invention, the surgical robot 102 is designed for performing minimally invasive surgical procedures. The surgical robot 102 is controlled by a user, optionally via a joystick, a mouse, a keyboard, or a combination thereof.

In an alternative embodiment of the present invention, the surgical robot 102 is not included in the system 100. Rather, the applicator 104 and catheter 106 are manipulated by the user in a different manner. For example, the applicator 104 and the catheter 106 may be manipulated directly by the user, or through other tools, which are available today or may be available in the future.

In some embodiments of the present invention, the catheter 106 generates radiation by electrical means, and radiation may be increased, decreased, and turned on and off by the user. An exemplary catheter includes a miniaturized x-ray tube with its requisite power supply and cooling system. Such a catheter may be referred to in the art as "radiation delivery arm".

Specific embodiments of the applicator 104 will be presented below.

Figures 2A, 2B:
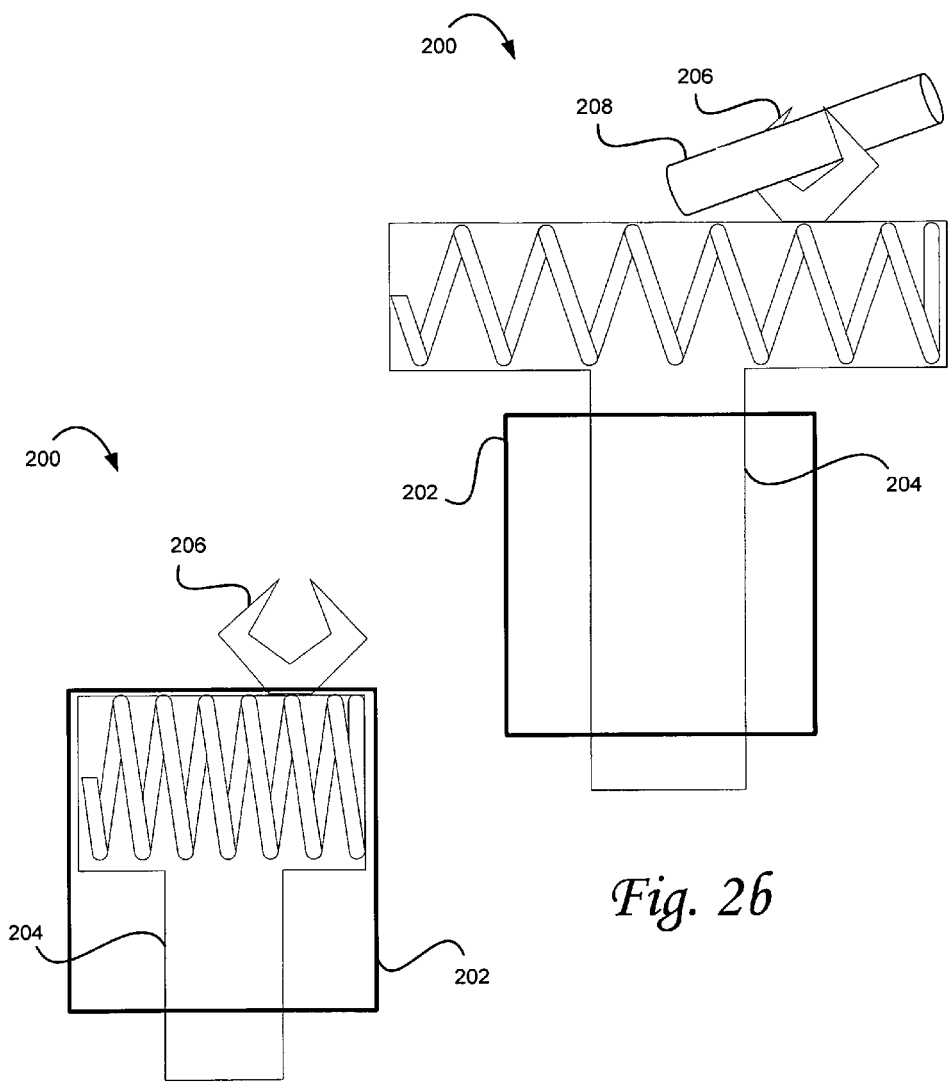
FIGS. 2a and 2b are schematic diagrams illustrating an applicator characterized by a spring mechanism, according to some embodiments of the present invention.

FIGS. 2a and 2b are schematic diagrams illustrating an applicator 200 characterized by a spring mechanism, according to some embodiments of the present invention. The applicator 200 is an embodiment of the applicator 104 of FIG. 1.

The applicator 200 includes a sheath 202, a spring mechanism 204, and a catheter grasper 206 attached to a distal end of the spring mechanism 204. FIG. 2a illustrates a closed configuration of the applicator 200. The spring mechanism 204 is held within the sheath 202, and pushes against inner walls of the sheath 202. The sheath 202 therefore limits the extension of the spring mechanism 204. In the closed configuration, the applicator 200 is compact, and therefore the size of the incision through which the applicator 200 is inserted into a cavity is decreased.

Once the applicator 200 is inserted into the cavity, a user may switch to an open configuration of the applicator 200, as shown in FIG. 2b. In the open configuration, the spring mechanism 204 is moved out of a distal end of the sheath 202, and without being restricted by the sheath 202, the spring mechanism 204 is released into a predetermined arrangement. Such an arrangement may, for example, allow the grasper 206 to be moved to a desired position, which was unattainable in the closed configuration. Once the grasper 206 is fixed in the desired position, a radiation delivery catheter 208 is moved into grasper 206, as explained in the description of FIG. 1.

Optionally, the spring mechanism 204 is designed to be moved in and out of a distal end of the sheath 202, by keeping the sheath 202 in a fixed position, and pushing and pulling the spring mechanism 204. Optionally or alternatively, the spring mechanism 204 is designed to be moved in and out of a distal end of the sheath 202, by keeping the spring mechanism 204 in a fixed position, and pushing and pulling the sheath 202.

The sheath 202 may be of any shape. In an exemplary embodiment of the present invention, the sheath is a capless cylinder. In another exemplary embodiment, the sheath is made of steel. Alternatively, the sheath may be made of aluminum or plastic.

The spring mechanism 204 may include a spring and a rod to push the spring along the sheath 202. As will be described below, the spring mechanism 204 may include one or more wire springs. The wire springs may be made of steel, or other suitable alloys.

According to some embodiments of the present invention, the grasper 206 is made of steel. In an exemplary embodiment of the present invention, the grasper is designed to hold a catheter having a diameter of about 2 mm. Optionally, the grasper 206 is adjustable for holding catheters having different diameters. The shape and properties of the grasper 206 do not affect the scope of the present invention, and any kind of grasper may be used as part of the applicator 200. According to some embodiments of the present invention, the grasper 206 is designed to hold a plurality of radiation delivery catheters. Optionally, the grasper 206 is configured to hold the catheter at any of a plurality of predetermined positions along the catheter. Optionally, more than one grasper is attached to the distal end of the spring mechanism 204. In a variant, the spring mechanism 204 may assume a plurality of arrangements on the open configuration, each arrangement corresponding to a predetermined radiation field, or a predetermined set of radiation fields.

According to some embodiments of the present invention, a mapping procedure is performed prior to the use of the applicator 200. In the mapping procedure, radiation fields are measured for each a plurality of arrangements of the applicator 200. For example, for each arrangement of the grasper or graspers in the open configuration, catheters are inserted into one, some, or all the rods. The different radiation fields are then measured, and matched to the arrangements. In addition, further arrangements are created, as the catheters are moved along the graspers to approach or move away from the target. The catheters are held by the graspers at different positions along the lengths of the catheters. The radiation fields corresponding such arrangements are also measured. Finally, if more than one catheter is present, some catheters may turned on and off at different times according to predetermined patterns. The radiation fields created by these patterns are measured, and matched to the patterns. A more detailed explanation of the mapping procedure is provided below, in the description of FIG. 13.

The mapping procedure is used for composing an atlas of a plurality of predetermined radiation field that may be delivered to the target via the applicator 200. In a radiation treatment procedure, a desired radiation field is chosen among the plurality of radiation fields within the atlas, according to at least one property of the target. Once the desired radiation field is chosen, the applicator 200 is set in the arrangement which corresponds to the desired radiation field, and the catheter or catheters are turned on and off according to the pattern which corresponds to the desired radiation field. In this manner, the desired radiation field is delivered to the target.

Figures 3A, 3B:
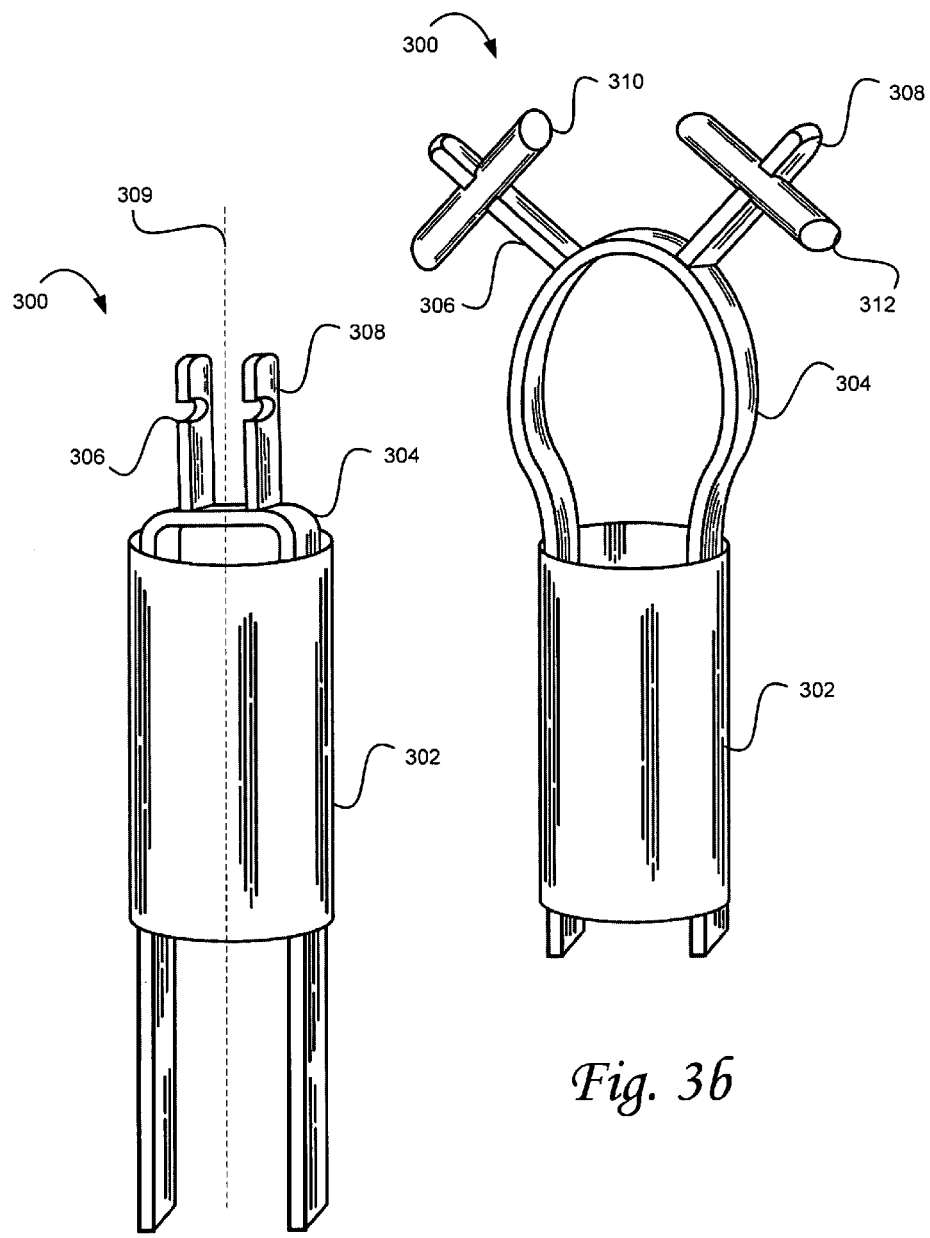
FIGS. 3a and 3b are perspective drawings illustrating an applicator characterized by a single spring wire, according to some embodiments of the present invention.

FIGS. 3a and 3b are perspective drawings illustrating an applicator 300 characterized by a single spring wire, according to some embodiments of the present invention. The applicator 300 is an embodiment of the applicator 200 of FIGS. 2a and 2b.

The applicator 300 includes a cylindrical sheath 302, a bent wire spring 304, a first catheter grasper 306 attached to a distal end of the wire spring 304, and second catheter grasper 308 attached to a distal end of the wire spring 304. The applicator 300 is similar to the applicator 200 of FIGS. 2a and 2b. The spring mechanism used in the applicator 300 is the bent wire spring 304. Optionally, the wire spring 304 is made of steel.

In FIG. 3a, the applicator 300 is in a closed configuration. The wire spring 304 is compressed by the inner walls of the sheath 302. In FIG. 3b, the wire spring is moved out of a distal side of the sheath 302 along a direction of a central axis 309 of the sheath, and a distal portion of the wire spring 304 expands and assumes a curved shape. In this manner, the graspers 306 and 308 are set into a predetermined arrangement with respect to each other and to the target. A first radiation delivery catheter 310 is moved into the first grasper 306 and a second radiation delivery catheter 312 is moved into the second grasper 308. The predetermined arrangement between the graspers 306 and 308, and therefore between the catheters 310 and 312, allows the delivery of a predetermined radiation field to the target, which is measured during a mapping procedure, as described above.

Optionally, the open configuration may allow for a plurality of predetermined arrangements. According to some embodiments of the present invention, the shape assumed by the wire spring 304 varies with the size of the portion of the wire spring 304 which is outside a distal end of the sheath 302. The shape of the wire spring 304 therefore affects the arrangements between the catheters 310 and 312 and the target, and each arrangement corresponds to one of or a set of a plurality if radiation fields. The radiation fields may be predetermined through the mapping procedure described above.

Figure 4A:
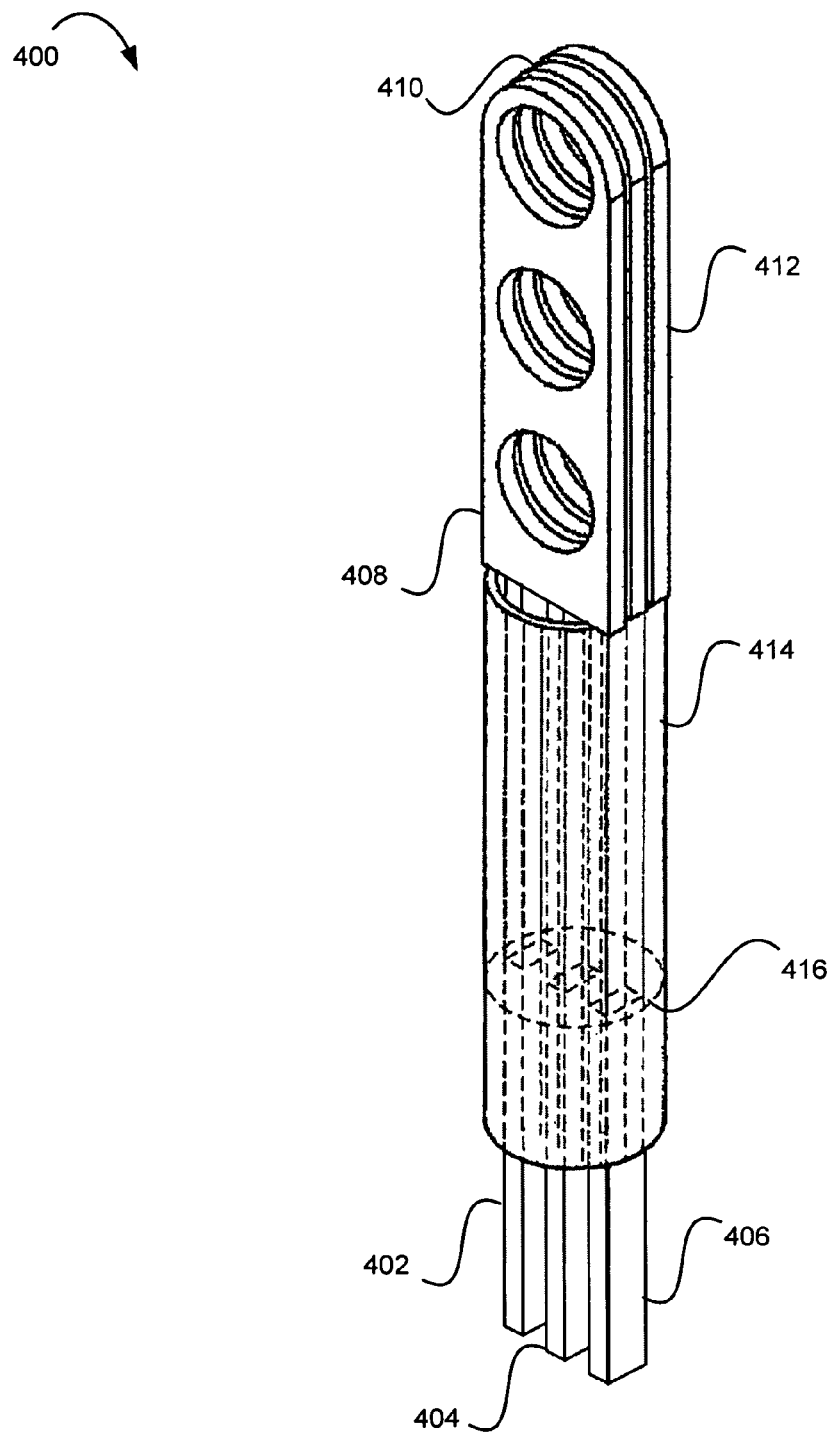
FIGS. 4a and 4b are schematic drawings illustrating a cross section of an applicator characterized by three wire springs, each wire spring holding a catheter grasper which may hold three catheters, according to some embodiments of the present invention.
Figure 4B:
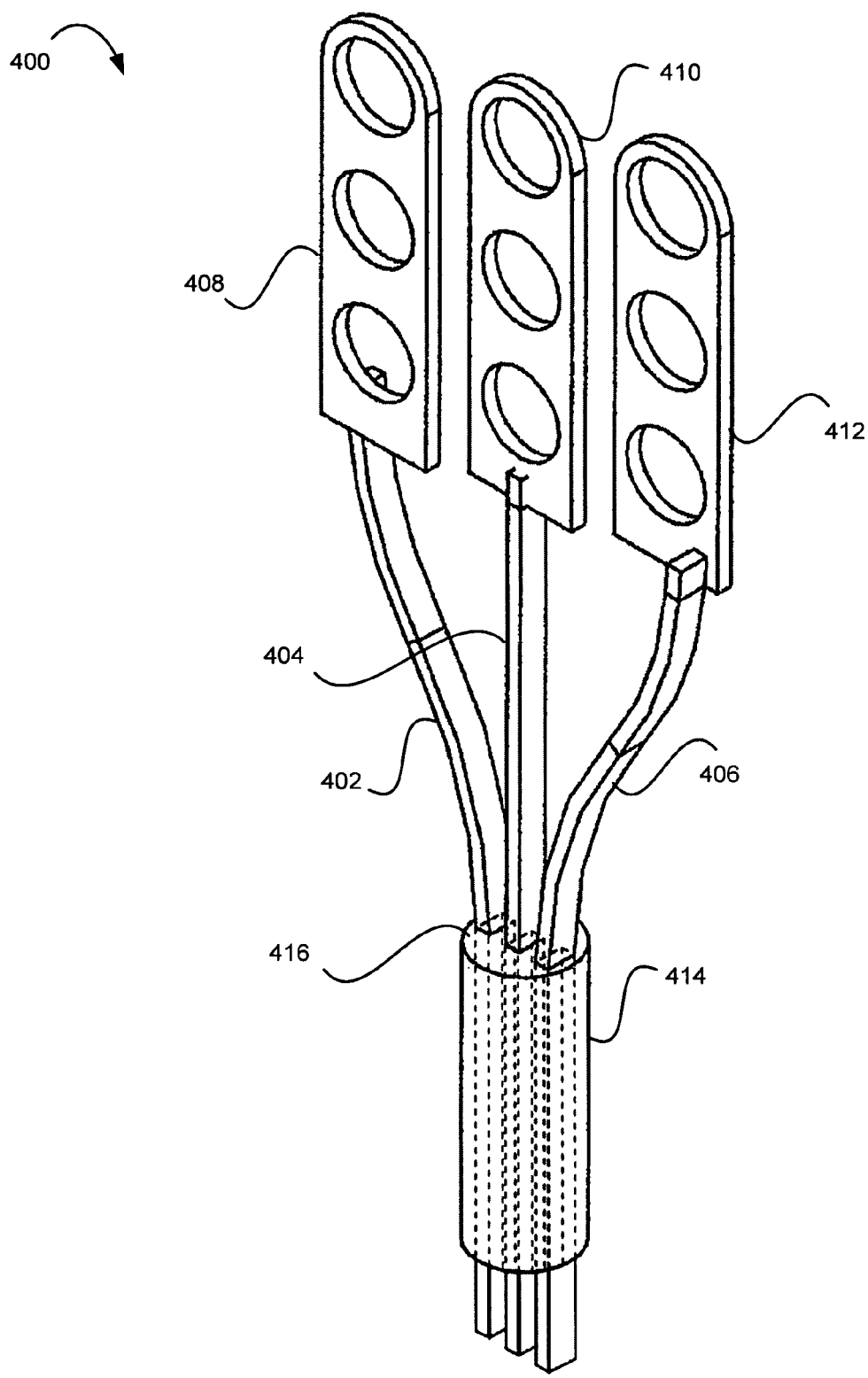

FIGS. 4a and 4b are perspective drawings illustrating an applicator 400 characterized by three wire springs, each wire spring holding a catheter grasper which may hold three catheters, according to some embodiments of the present invention. The applicator 400 is an embodiment of the applicator 200 of FIGS. 2a and 2b.

In the applicator 400, the spring mechanism includes three wire springs 402, 404, and 406. Three graspers, 408, 410, and 412 are attached to the distal ends of the wire springs 402, 404, and 406, respectively. Each grasper is characterized by three orifices, and is therefore designed to hold up to three radiation delivery catheters.

In FIG. 4a, a closed configuration of the applicator 400 is illustrated: the wire springs 402, 404, and 406 springs are inside a sheath 408, and the graspers 408, 410, and 412 are bunched together. In the close configuration, the applicator 400 is compact, and therefore easy to insert into a cavity via a small incision.

In FIG. 4b, an open configuration of the applicator 400 is illustrated: the wire springs 402, 404, and 406 are moved out of a distal end of the sheath 408, and are released into a predetermined arrangement. The graspers 408, 410, and 412 are elongated panels each having three orifices, each orifice designed for receiving a catheter. In this manner, the graspers form a 3×3 grid of catheter receiving orifices, allowing the insertion of up to nine catheters. A user may deliver a desired radiation field to the target, by choosing a desired number of catheters inserted into desired orifices, and turning on each catheter for a desired period of time. The above choices allow a plurality of radiation fields to be applied to the target with the help of the applicator 400, and a desired radiation field may be chosen according to at least one property of the target.

According to some embodiments of the present invention, the middle wire spring 404 is a straight wire, which does not form a curved shape, when moved out of the distal end of the sheath 414. Optionally, a different number of wire springs, such as 2, 4, 5, for example, is used in the applicator 400. Optionally, differently shaped graspers are used. Optionally, the graspers are designed for holding a different number of catheters, such as 1, 2, 5, 6, for example.

According to some embodiments of the present invention, the applicator 400 includes an anchor 416. The anchor 416 is an element attached to the wire springs, and is designed for keeping a distance between the wire springs fixed at an anchoring location along the wire springs. The anchor 416 moves with the wire springs along a direction of the central axis of the sheath 414. In the exemplary embodiment illustrated in FIGS. 4a and 4b, the anchor 416 is a disk characterized by three holes, each hole configured for being traversed by and welded to one of the wire springs. The anchor 416 ensures that the distance between the wire springs at the anchoring position is fixed. This ensures that the arrangement of the wire springs does not change, when the wire springs are moved out of the distal end of the sheath 414. Therefore, a user knows that the arrangement of the wire springs is the same, when the anchor 416 is at a specific location along the length of the sheath 414. In this manner, the arrangement of wire springs, and consequently the predetermined radiation fields are repeatable.

Optionally, the diameter of the disk-shaped anchor 416 is about equal to the diameter of the inner wall of the sheath 414. This ensures that the wire do not move toward the sides of the sheath 414 at the anchoring position, and therefore the distance between the wires and the sheath 414 at the anchoring position is fixed as well. In this manner, the repeatability of the predetermined radiation fields is further enhanced.

In some variants, proximal sections of the wire springs are joined together, and form a rigid body called a wire mesh, which makes it easier for a user to move the wire springs along the sheath 414, and ensures that all the wire springs are moved together along a direction of a central axis of the sheath 414. According to some embodiments of the present invention, the portions of the wire springs that are proximal of the anchor 416 are fastened to each other, while the portions of the wire springs that are distal of the anchor 416 are separate from each other. Optionally, the proximal portions of the wire springs of are joined to each other by being welded together. Alternatively, the proximal portions of the wire springs of are joined to each other by being glued to each other.

In the exemplary embodiment of FIGS. 4a and 4b, the manner in which the graspers are attached to the wire springs deserves some attention. The grasper 408 is attached to a front surface of the of the wire spring 402; the middle grasper 410 is welded onto the middle of the central wire spring 404; the grasper 412 is attached to a back surface of the wire spring 406. In this manner, when the spring wires are fully retracted into the sheath 414, the graspers are offset from each other and therefore do not bump into each other, but are ordered side by side in the compact configuration shown in FIG. 4a.

In some variants, the spring wires assume a plurality of arrangements within the open configuration of the applicator 400. As the spring wires are moved further and further out of the distal end of the sheath 414, the sheath 414 limits the releasing of the spring wires less and less. In an exemplary embodiment, a different arrangement of the spring wires is achieved at each different position of the anchor 416 along the sheath 414.

Figures 5A, 5B:
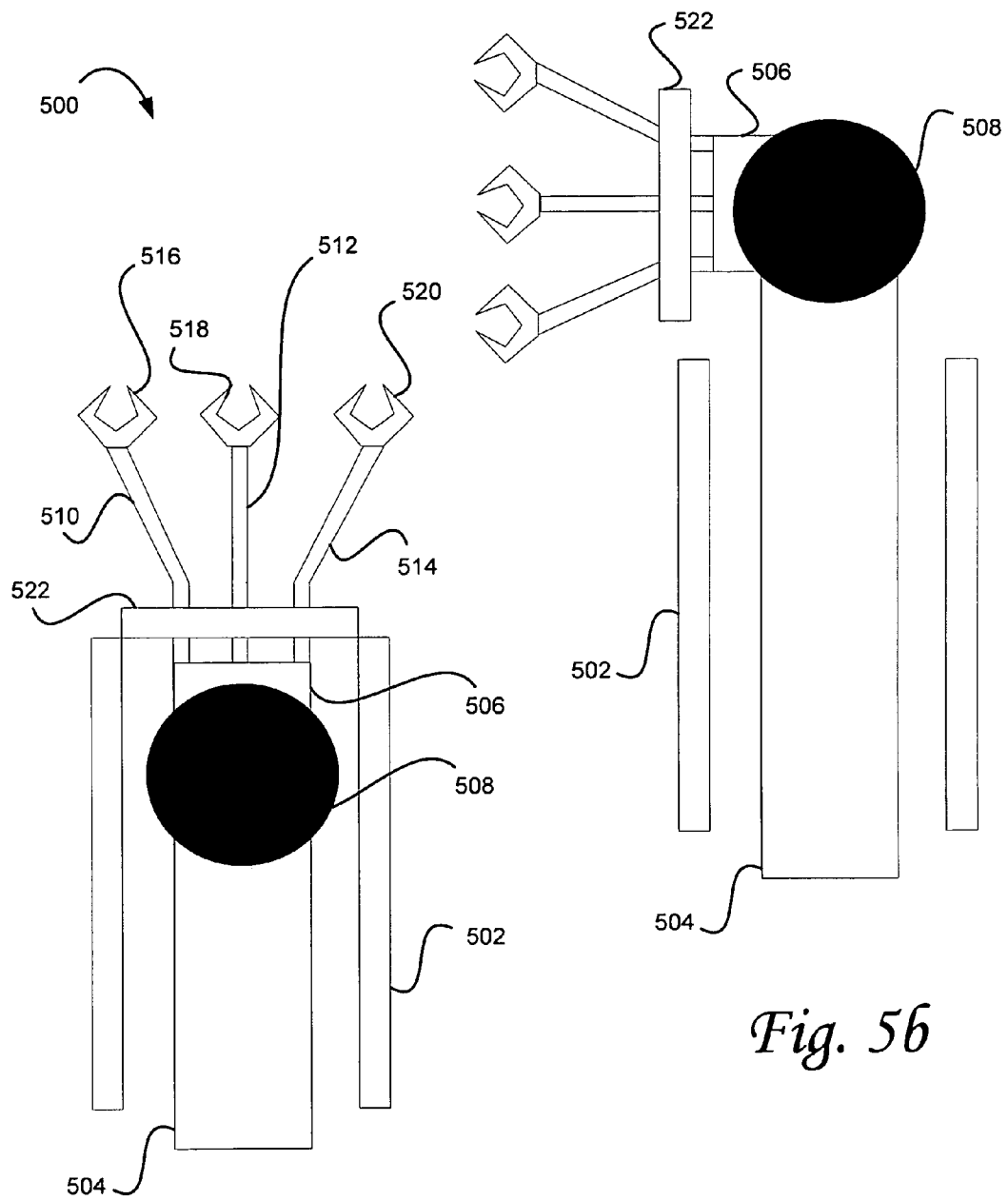
FIGS. 5a and 5b are perspective drawings illustrating an applicator characterized by a hinging mechanism designed to rotate the wire springs in an open configuration about an axis perpendicular to a central axis of the sheath, according to some embodiments of the present invention.

FIGS. 5a and 5b are schematic drawings illustrating a cross section of an applicator 500 characterized by a hinging mechanism designed to rotate the wire springs in an open configuration about an axis perpendicular to a central axis of the sheath, according to some embodiments of the present invention. The applicator 500 is an embodiment of the applicator 200 of FIGS. 2a and 2b.

The applicator 500 includes a sheath 502, a proximal wire mesh section 504, a distal wire mesh section 506, and a hinging mechanism 508 connected to the wire mesh sections 504 and 506. Three wire springs 510, 512, and 514 extend from a distal end of the distal wire mesh section 506, and are attached to the catheter graspers 516, 518, and 520, respectively. Optionally, the applicator 500 further includes an anchor 522, which is similar to the anchor 416 of FIGS. 4a and 4b.

The hinging mechanism 508 is controllable by a user to rotate the distal wire mesh section 506 with respect to a central axis of the proximal wire mesh section 504. As the hinging mechanism 508 rotates the distal wire mesh section 506, the wire springs 510, 512, and 514 and the catheter graspers 516, 518, and 518 are also rotated with respect to the central axis of the proximal wire mesh section 504. Because of the inclusion of the hinging mechanism 508, the applicator 500 may reach areas within a cavity, which may not be reached by moving the whole applicator 500 within the cavity, or areas that may be reached through complicated maneuvers by the user.

Optionally, the rotation of the distal wire mesh 506 along the hinging mechanism 508 is continuous, and the user may stop the rotation at any angle within a predetermined range. Alternatively, the hinging mechanism 508 is designed to allow the rotation to stop at discrete angles. According to some embodiments of the present invention, the hinging mechanism 508 is controlled by the user via an arm of the surgical robot.

Figures 6A, 6B:
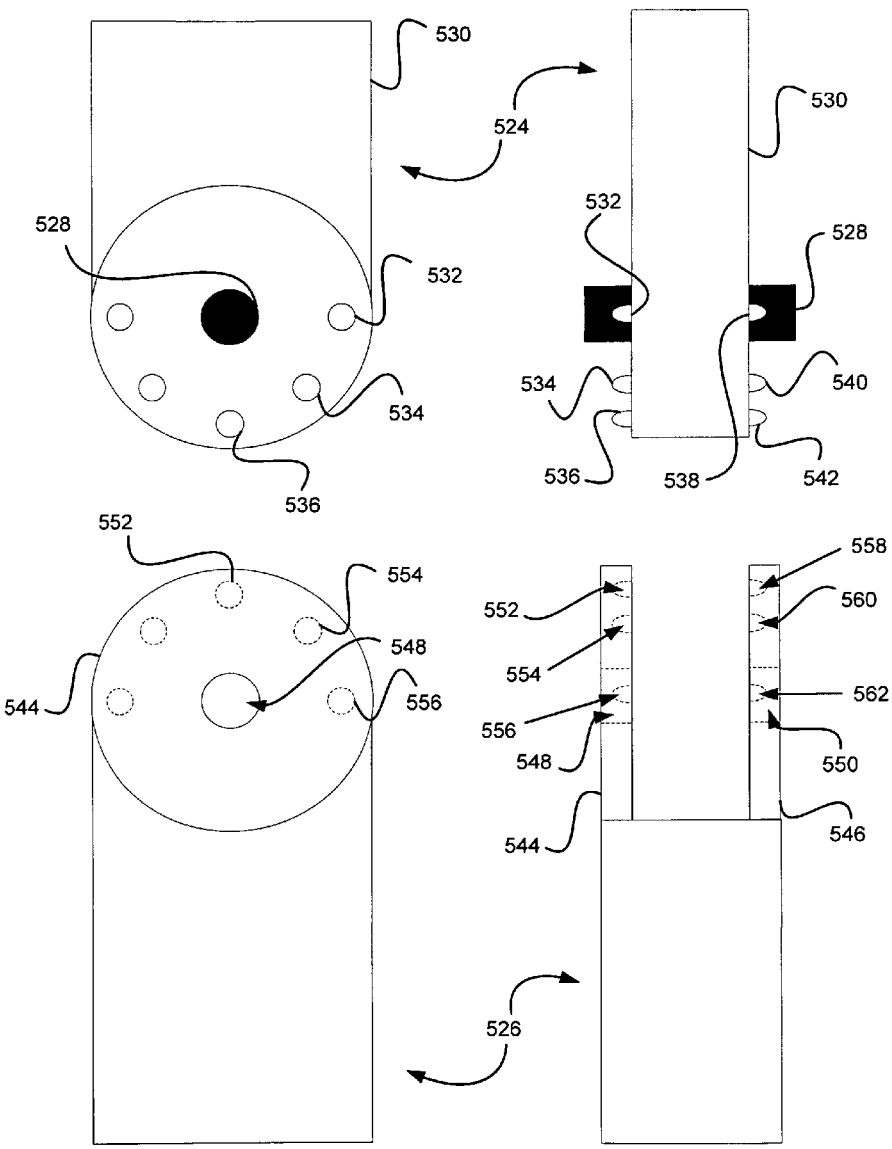
FIGS. 6a and 6b are schematic drawings illustrating an exemplary hinging mechanism, according to some embodiments of the present invention.

FIGS. 6a and 6b are schematic drawings illustrating an exemplary hinging mechanism, according to some embodiments of the present invention. FIG. 6a illustrates a front view of the hinging mechanism, and FIG. 6b illustrates a side view of the hinging mechanism.

The hinging mechanism includes a male section 524 and a female section 526. The male section 524 includes a cylindrical pinwheel 528 traversing a main body 530 of the male section 524 from side to side, and extending beyond the sides of the main body 530. On two sides of the main body 530 of the male section 524, are provided balls, such as the balls 532, 534, 536, 538, 540, and 542. The balls are spring loaded, so they retract within the main body 530, when no space is available, and spring out of the main body 530, when space is available.

The female section 526 is characterized by two side pieces 544 and 546, each configured to be adjacent to one of the sides of the main body 530 of the male section 524. The side pieces 544 and 546 are characterized by orifices 548 and 550, respectively, both designed for being traversed by the pinwheel 528. The left side piece 544 is further characterized by cup grooves, such as the cup grooves 552, 554, and 556. The right side piece 546 is characterized by cup grooves such as the cup grooves 558, 560, and 562. When a ball, such as the ball 532, touches an inner wall of the left side piece 544, the ball is retracted within the main body 530 of the male section 524.

As the male section 524 and female section 526 are rotated with respect to each other about a central axis of the pinwheel 528, a balls will reach cup grooves—for example, the ball 536 reaches the cup groove 552. When this happens, the ball 536 springs up and is held by the cup groove 552. In this manner, the rotation is stopped, and may be resumed by the application of a force by a user. The balls and cup grooves are set up, so that the male section 524 and female section 526 of the hinging mechanism may be held at a plurality of selected angles with respect to each other—for example, at angles of about ±45, 90 degrees. It should be noted that the technical details of the hinging mechanism do not affect the usefulness of the present invention, and different types of hinging mechanisms may be used.

Referring back to FIGS. 5a and 5b, optionally, the male section 524 of the hinging mechanism 508 is attached to the distal wire mesh section 506, while the female section 526 of the hinging mechanism 508 is attached to the proximal wire mesh section 504. Alternatively, the male section 524 of the hinging mechanism 508 is attached to the proximal wire mesh section 504, while the female section 526 of the hinging mechanism 508 is attached to the distal wire mesh section 506.

Figure 7:
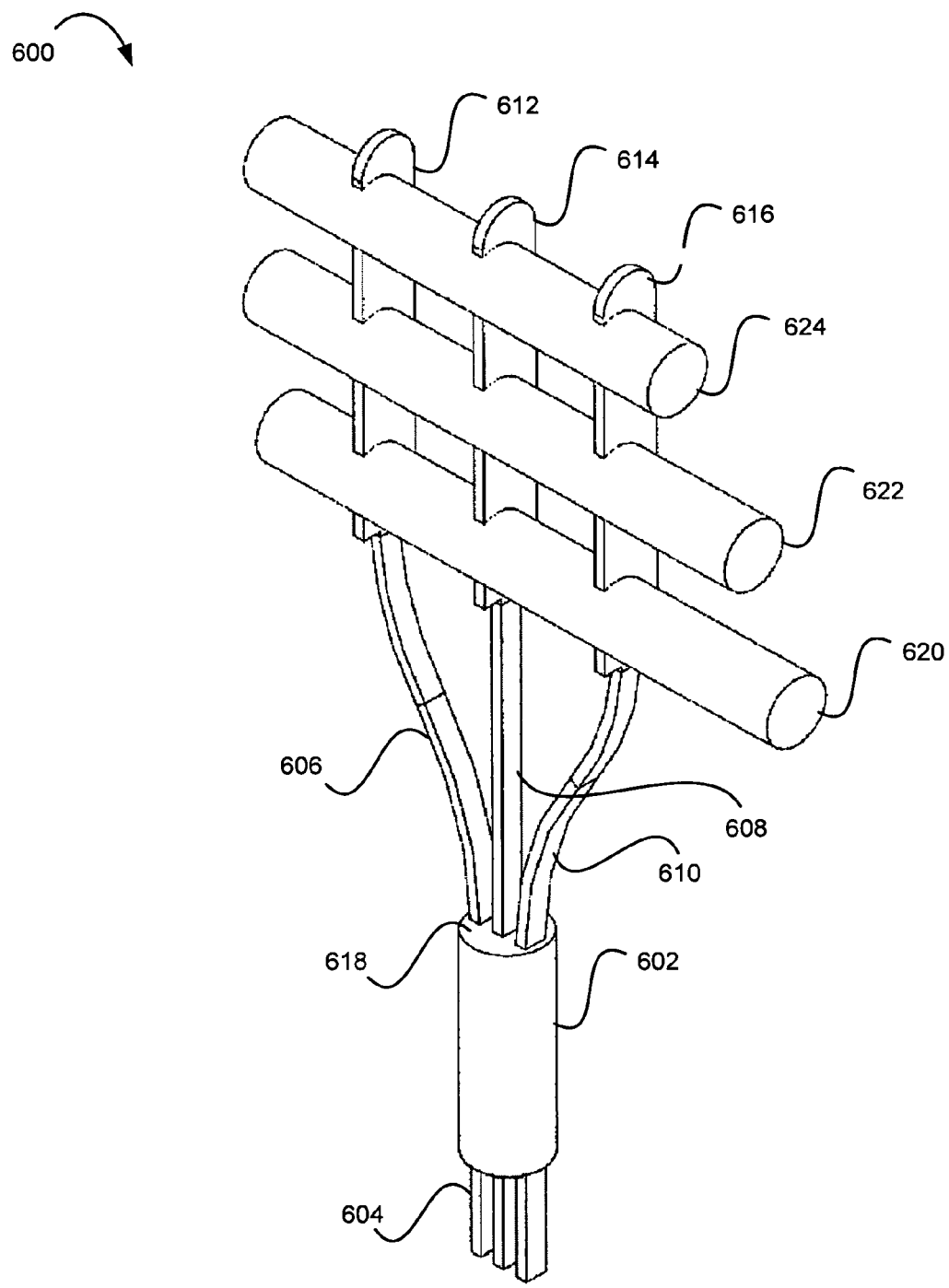
FIG. 7 is a perspective drawing illustrating an applicator having catheter graspers holding different portions of the same catheter, according to some embodiments of the present invention.

FIG. 7 is a perspective drawing illustrating an applicator 600 having catheter graspers holding different portions of the same catheter, according to some embodiments of the present invention. The applicator 600 is an embodiment of the applicator 200 of FIGS. 2a and 2b.

The applicator 600 is very similar to the applicator 400 of FIGS. 4a and 4b. The applicator 600 includes a sheath 602 housing a wire mesh 604. The wire mesh 604 includes three wire springs 606, 608, and 610 joined together at proximal sections thereof. The three wire springs 606, 608, and 610 are separate from each other at distal sections thereof, and are attached at distal ends thereof to catheter graspers 612, 614, and 616, respectively. Optionally, the applicator 600 includes an anchor 618. In some variants, the applicator 600 includes a hinging mechanism, like the hinging mechanism 508 of FIGS. 5a and 5b.

A difference between the applicator 600 and the applicator 400 lies in the shape and setup of the catheter graspers 612, 614, and 616. Each of the graspers 612, 614, and 616 is an elongated panel characterized by three openings, each opening designed to hold a section of a catheter. In the open configuration of the applicator 600, the graspers are configured so that a single catheter is held by three different graspers. Each one of the catheters 620, 622, and 624 is held by all graspers 612, 614, and 616. The catheters therefore, set along a plane, which is parallel to the central axis of the sheath 602.

Such a setup may be used to aim catheters at a target located at a side of the applicator 600. The radiation field may be varied by adding or removing catheters, moving the catheters along the graspers toward or away from the target, and/or by turning the different catheters on for selected periods of time.

The applicator 600 may be characterized by any number of wire springs. The graspers 612, 614, and 616 may be characterized by any number of openings.

Figure 8:
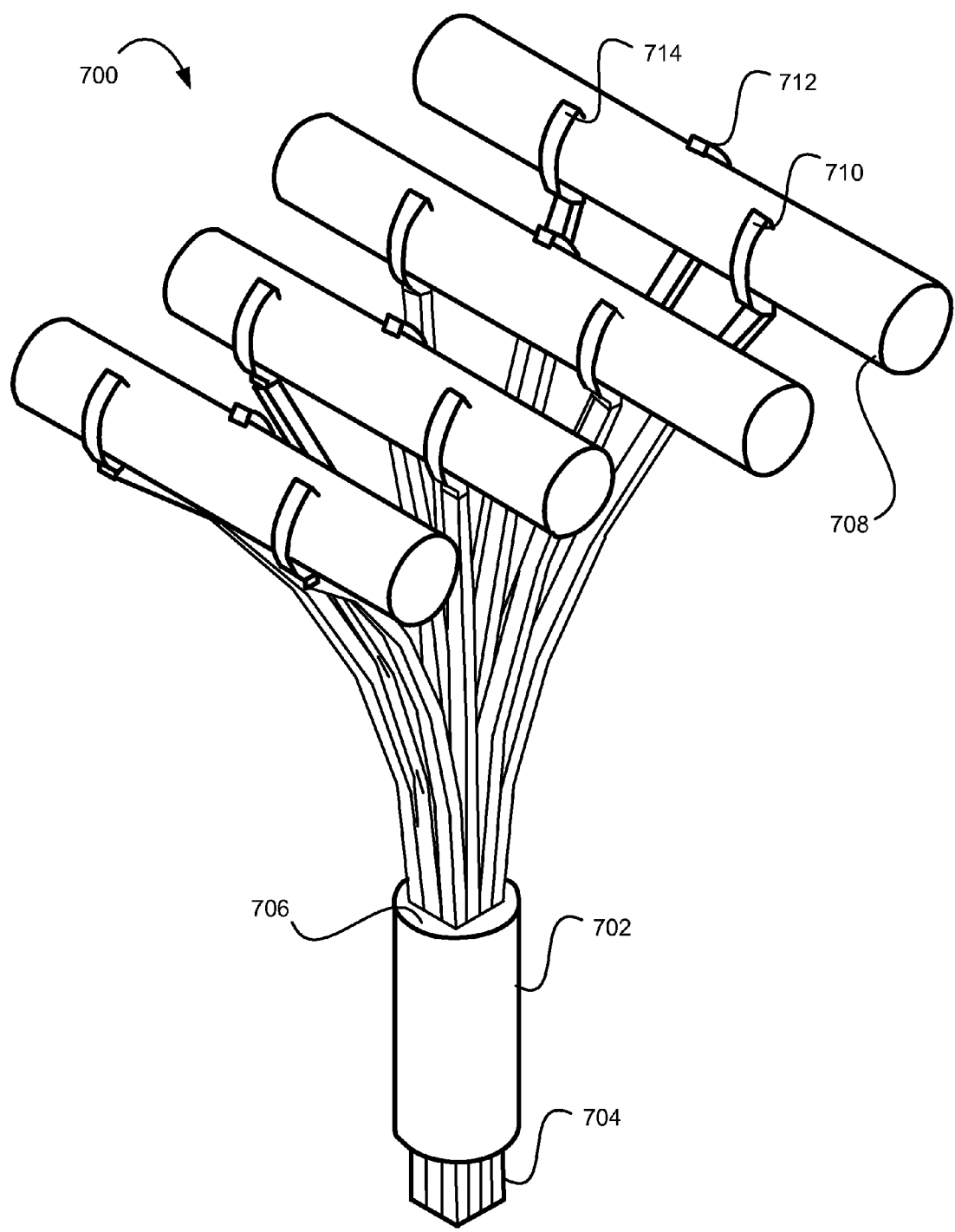
FIG. 8 is a perspective drawing illustrating an applicator in which each catheter is held by two catheter graspers, according to some embodiments of the present invention.

FIG. 8 is a perspective drawing illustrating an applicator 700 in which each catheter is held by two catheter graspers, according to some embodiments of the present invention. The applicator 700 is an embodiment of the applicator 200 of FIGS. 2a and 2b.

The applicator 700 is very similar to the applicator 400 of FIGS. 4a and 4b. The applicator 700 includes a sheath 702 housing a wire mesh 704. The wire mesh 704 includes a plurality of wire springs joined together at proximal sections thereof. The wire springs are separate from each other at distal sections thereof, and are attached at distal ends thereof to catheter graspers. Each wire spring is designed to hold a single catheter grasper, and each grasper is designed to hold a section of a single catheter. Optionally, the applicator 700 includes an anchor 706. In some variants, the applicator 700 includes a hinging mechanism, like the hinging mechanism 508 of FIGS. 5a and 5b.

In the applicator 700, each grasper is designed to hold a section of a catheter, and the wire springs are set up so that one catheter is held by a plurality of graspers. For example, the catheter 708 is held by three graspers 710, 712, and 714. The catheter graspers are curved elongated panels, each designed to encircle and grip a single section of a catheter. In some variants of the present invention, catheters are held parallel to each other and set on a plane perpendicular the central axis of the sheath 702.

Optionally, a distance between the graspers varies according to a length of wire spring sections that are outside a distal end of the sheath 702. For example, as the wire springs are moved more and more out of the distal end of the sheath 702, a length of the sections that are outside of the distal end of the sheath 702 grows, the wire springs release more, and a distance between at least two sets of graspers configured to hold two catheters grows. As the distance between graspers varies, a distance between at least two catheters varies as well, and therefore a plurality of arrangements may be achieved.

The radiation field may be varied by adding or removing catheters, moving the catheters along the graspers toward or away from the target, and/or by turning the different catheters on for selected periods of time. The applicator 700 may be characterized by any number of wire springs.

Figure 9A:
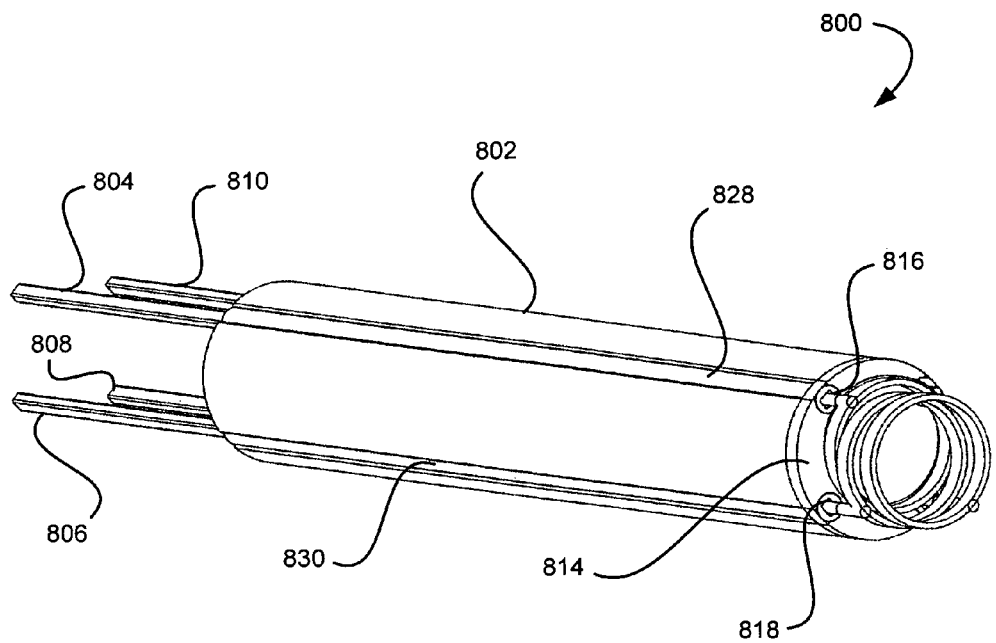
FIGS. 9a and 9b are perspective drawings illustrating an applicator characterized by four wire springs, each wire spring holding a loop-shaped catheter grasper, according to some embodiments of the present invention.
Figure 9B:
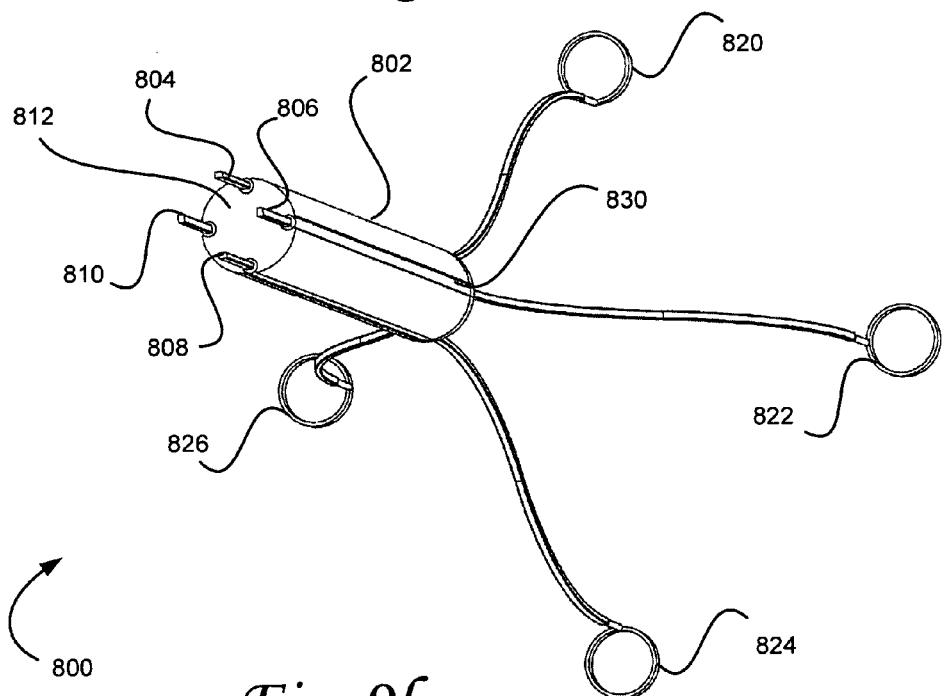

FIGS. 9a and 9b are perspective drawings illustrating an applicator 800 characterized by four wire springs, each wire spring holding a loop-shaped catheter grasper, according to some embodiments of the present invention. The applicator 800 is an embodiment of the applicator 200 of FIGS. 2a and 2b.

The applicator 800 includes a sheath 802, which houses four wire springs 804, 806, 808, and 810. The wire springs are the spring mechanism 204 of FIGS. 2a and 2b. According to some embodiments of the present invention, the sheath 802 is a cylinder which includes a proximal cap 812 and a distal cap 814. Each of the caps of the sheath 802 is characterized by four holes, such 816 and 818. Each wire spring enters the sheath 802 through a hole on the proximal cap 812, and exits the sheath 802 through a hole on the distal cap 814. The distal ends of the wire springs 804, 806, 808, and 810 are attached to catheter graspers 820, 822, 824, and 826, respectively.

Optionally, the catheter graspers 820, 822, 824, and 826 are loops, each designed to encircle and grip a single catheter.

In FIG. 9a, the applicator 800 is in a closed configuration. The wire springs 804, 806, 808, and 810 are retracted within the sheath 802, so that only distal ends of the wire springs extend out of the distal cap 814. The graspers 820, 822, 824, and 826 are set side by side: a distal side of the first grasper 820 touches a proximal side of the second grasper 822; a distal side of the second grasper 822 touches a proximal side of the third grasper 824; a distal side of the third grasper 824 touches a proximal side of the fourth grasper 826. In such a manner, the applicator 800 is in a compact configuration, and therefore a size of the incision through which the applicator 800 enters a cavity is decreased.

In FIG. 9b, the applicator 800 is in an open configuration. The wire springs 804, 806, 808, and 810 are moved along the sheath 802, out of the distal cap 814. The wire springs 804, 806, 808, and 810 are no longer bound by the sheath 802, are therefore released into a predetermined arrangement.

Optionally, the wire springs 804, 806, 808, and 810 are moved together. Alternatively, each wire spring is moved individually. In some variants, the wire springs expand more, as larger sections thereof are moved outside the sheath 802, out of the distal cap 814. Therefore, different arrangements are defined by the distance of the wire springs portions that are distal of the distal cap 814. Once a chosen arrangement is achieved, catheters are moved through one, some, or all the graspers, and a predetermined radiation field is applied to a target area in the manner described above.

According to some embodiments of the present invention, the sheath 802 includes channels, each channel designed for being traversed by one individual wire spring. For example, a first channel 828 is traversed by the wire spring 804, and a second channel 830 is traversed by the wire spring 806. The channels have a cross sectional area which is slightly larger than the cross sectional area of the wire springs. The channels therefore keep the wire springs straight within the sheath 802, and limit the release of wire springs inside the sheath 802. The release of the wire springs inside the sheath 802 may cause the wire springs to exit the whole is an unpredictable manner, and may lower the repeatability of predetermined wire spring arrangements.

Figures 10A, 10B:
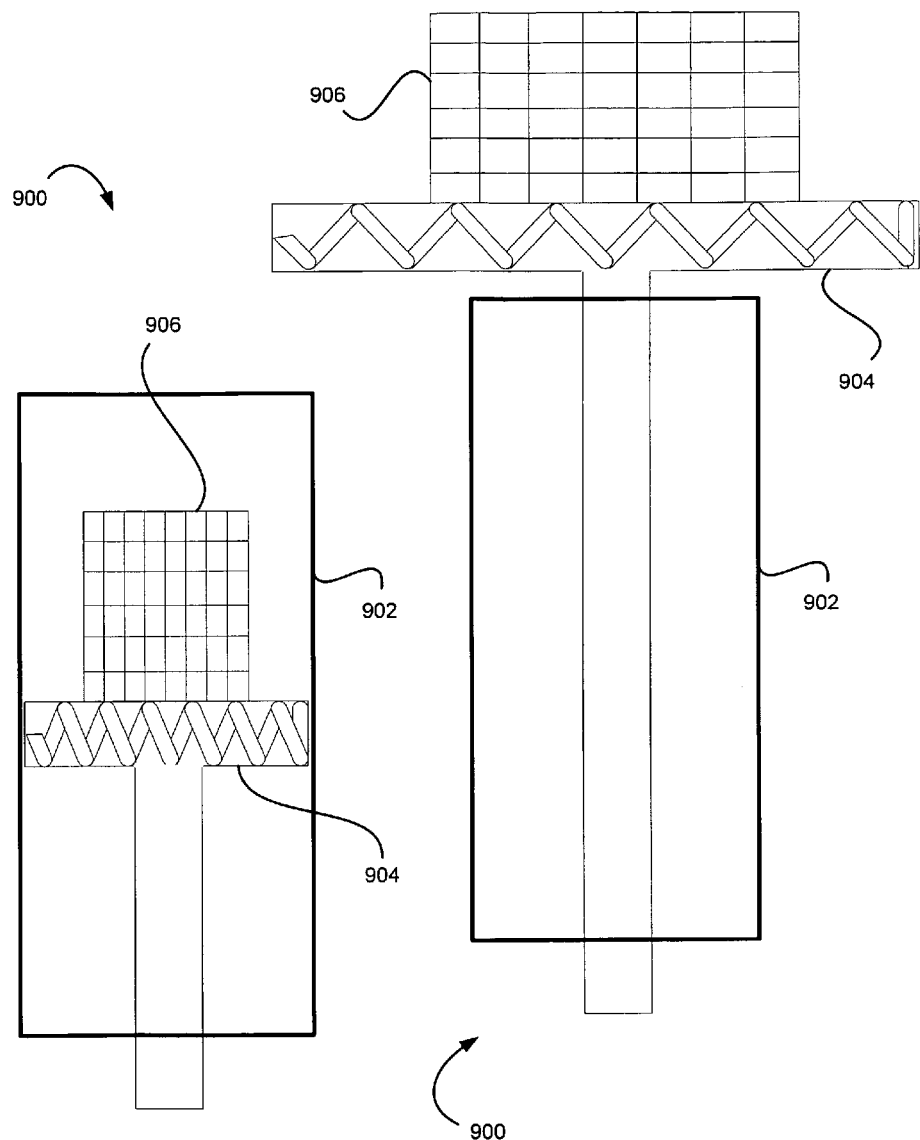
FIGS. 10a and 10b are schematic diagrams illustrating a device for aiming a radiation field toward a target area, the device being characterized by a film and a spring mechanism, according to some embodiments of the present invention.

FIGS. 10a and 10b are schematic diagrams illustrating a device 900 for aiming a radiation field toward a target area, the device being characterized by a film and a spring mechanism, according to some embodiments of the present invention.

The device 900 includes a sheath 902, a spring mechanism 904, and a film 906 attached to a distal end of the spring mechanism 904. The sheath 902 and spring mechanism 904 have the same properties as the sheath 202 and the spring mechanism 204 of FIGS. 2a and 2b. In FIG. 10a, a closed configuration of the device 900 is shown. The spring mechanism 904 and the film 906 are contained within the sheath 902. Optionally, only the spring mechanism 904 is contained within the sheath 902. In the closed configuration the inner walls of the sheath 902 limit the expansion of the spring mechanism 904, and the film 906 is not stretched. The closed configuration is used when the device 900 is inserted into a cavity through a port.

In FIG. 10b, an open configuration of the device 900 is shown. The spring mechanism 904 is moved out of a distal end of the sheath 902, and is no longer limited by a size of the sheath 902. The spring mechanism 904, therefore, is released into a predetermined arrangement. As the spring mechanism 904 extends, the film 906 is stretched to reach a surface, which encompasses the target area. The film 906 is designed to be applied onto the target area.

Optionally, the spring mechanism 904 is designed to be moved in and out of a distal end of the sheath 902, by keeping the sheath 902 in a fixed position, and pushing and pulling the spring mechanism 904. Optionally or alternatively, the spring mechanism 904 is designed to be moved in and out of a distal end of the sheath 902, by keeping the spring mechanism 904 in a fixed position, and pushing and pulling the sheath 902.

The film 906 is characterized by markings forming a grid. Once applied to the target area, the grid divides the target area into sub-areas. This division is useful for aiming an appropriate radiation field towards the target area, by moving a radiation delivery catheter to the proximity of selected sub-areas and applying a selected radiation to the selected sub-areas, as described in the method 1300 depicted in FIG. 14. The device 900 is controlled by a user, optionally via a surgical robot. The movement of the catheter is also controlled by the user, optionally via the surgical robot.

The film 906 is optionally transparent or semi-transparent, so that the target area is still visible when covered by the film 906. The film 906 may be made by materials such as cellophane or other flexible polymers. In an exemplary embodiment of the present invention, the sub-areas defined by the grid are squares having sides of 5 mm. The size of the sub-areas may be varied, according to the clinical situation.

Figures 11A, 11B:
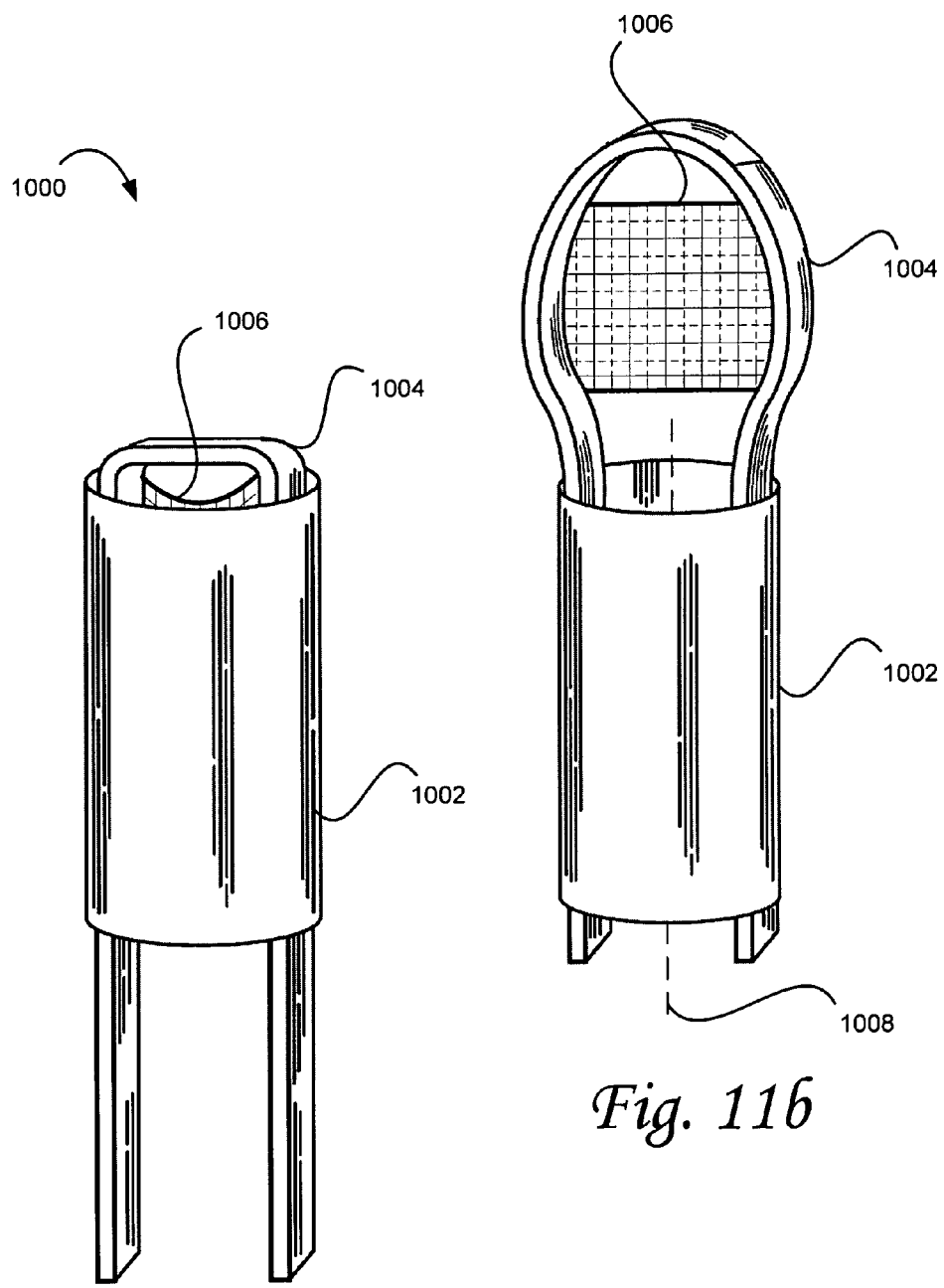
FIGS. 11a and 11b are perspective drawings illustrating a device for aiming a radiation field toward a target area, the device being characterized by a single spring wire, according to some embodiments of the present invention.

FIGS. 11a and 11b are perspective drawings illustrating a device 1000 for aiming a radiation field toward a target area, the device being characterized by a single spring wire, according to some embodiments of the present invention. The device 1000 is an embodiment of the device 900 of FIGS. 9a and 9b.

The device 1000 includes a sheath 1002, a wire spring 1004, and a film 1006 attached to at least two sides of the wire spring 1004. In the device 1000, the wire spring 1004 is the spring mechanism 904 of FIGS. 9a and 9b.

In FIG. 11a, the device 1000 is in a closed configuration. The wire spring 1004 is compressed by the inner walls of the sheath 1002, and the film is not stretched. In FIG. 10b, the wire spring is moved out of a distal side of the sheath 1002 along a direction of a central axis 1008 of the sheath 1002, and a distal portion of the wire spring 1004 expands and assumes a curved shape. In this manner, the distance between the sides of the wire spring 1004 grows, and the film 1006 is stretched. The delivery of a predetermined radiation field to the target is performed according to the method 1300 of FIG. 14.

Optionally, the sheath 1002 is a steel capless cylinder. Optionally the wire spring 1004 is made of steel.

Figure 12A:
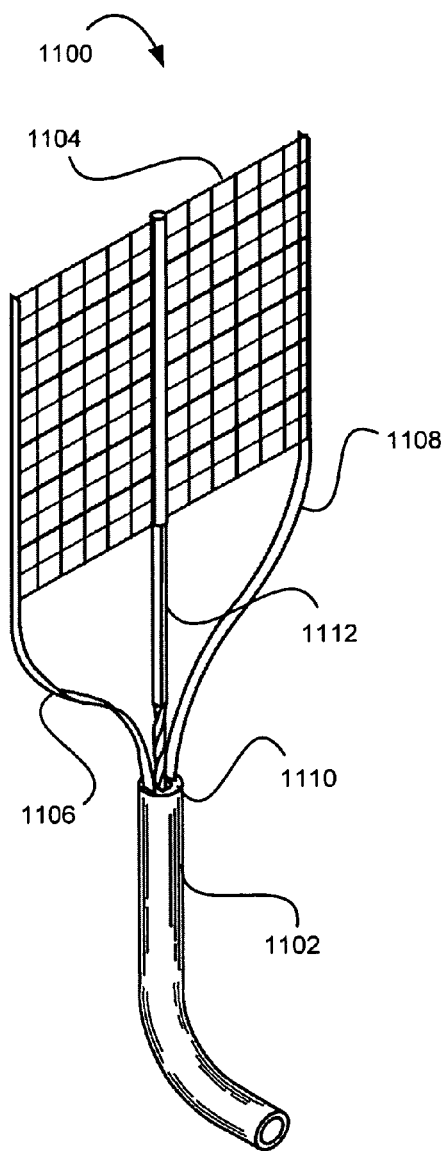
FIGS. 12a and 12b are perspective drawings illustrating a device for aiming a radiation field toward a target area, the device being characterized by two spring wires, according to some embodiments of the present invention.
Figure 12B:
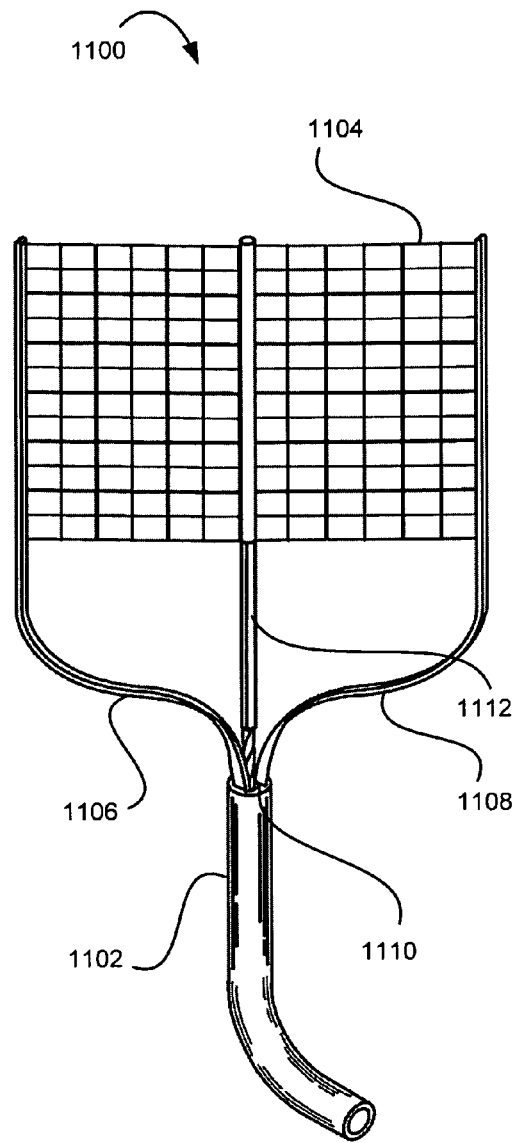

FIGS. 12a and 12b are perspective drawings illustrating a device 1100 for aiming a radiation field toward a target area, the device being characterized by two spring wires, according to some embodiments of the present invention. The device 1100 is an embodiment of the device 900 of FIGS. 10a and 10b.

Like the device 900, the device 1100 includes a sheath 1102, and a film 1104 characterized by markings forming a grid. In the device 1100, the spring mechanism includes a left wire spring 1006 and a right wire spring 1008, and the film 1004 is attached to the left and right wire springs 1006 and 1008.

The device 1100 is characterized by an open and a closed configuration. In the closed configuration, the wire springs 1006 and 1008 are close together. In the open configuration, the wire springs 1006 and 1008 are released into curved shapes, and distal sections of the wire springs 1006 and 1008 move apart from each other, thereby stretching the film 1008.

According to some embodiments of the present invention, proximal sections of the wire springs 1006 and 1008 are joined together into a wire mesh, as described above, in the section relating to FIGS. 4a and 4b. Optionally, the device 1100 includes an anchor 1110, with the same characteristics of the anchor 416 of FIGS. 4a and 4b.

In some variants of the present invention, the device 1100 further includes a middle wire 1112. Optionally, the middle wire 1112 is a straight wire and does not assume a curved shape, when moved out of a distal end of the sheath 1102. The middle wire 1112 is also attached to the film 1104.

According to some embodiments of the present invention, the middle wire 1112 may be controllably rotated by a user around a central axis of the middle wire 1112. As the middle wire 1112 is rotated, a central section of the film 1104 is pulled by the middle wire 1112 and rotated as well, thereby pulling and bending the left and right wires 1006 and 1008, as shown in FIG. 12b. In this manner the film 1104 may be rotated towards the target without a need to move the whole device 1100. This may be useful in situations in which moving the device 1100 as a whole toward a target is not feasible or requires complex maneuvering.

Optionally, the middle wire 1112 is spring loaded and rotates clockwise or counterclockwise, according to whether the middle wire 1112 is moved in or out of a distal end of the sheath 1102. In the closed configuration of the applicator 1100, the film 1104 is wrapped around the middle wire 1112. As the middle wire is moved out of the distal end of the sheath 1102, the rotation of the middle wire 1102 unfurls the film 1104, so that the film 1104 is stretched in the open configuration of the applicator 1100. Similarly, when the middle wire 1102 is retracted into the sheath 1102, the rotation of the middle wire 1102 causes the film 1104 to be wrapped around the middle wire 1102. In this manner, the film 1104 does not hang loosely from the wire springs 1006 and 1008. A loosely hanging film may become crumpled and ruined during the manipulation of the applicator 1002, or may get stuck within the cavity, making the applicator 1100 hard to remove from the cavity through a small incision.

Figure 13:
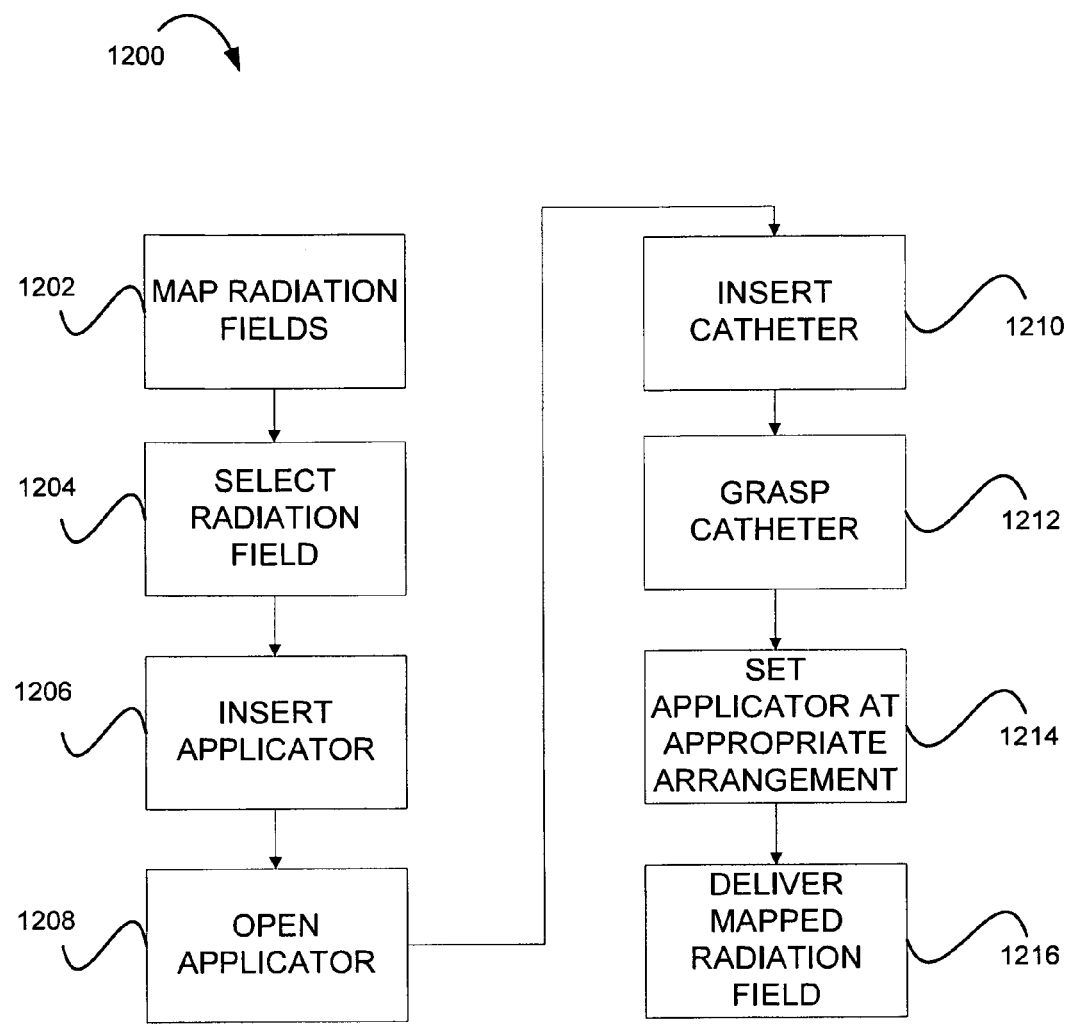
FIG. 13 is a flowchart illustrating a method for delivering a radiation field to a target through an applicator, according to some embodiments of the present invention.

FIG. 13 is a flowchart illustrating a method 1200 for delivering a radiation field to a target through an applicator, according to some embodiments of the present invention.

At 1202 a plurality of radiation fields is mapped. In the mapping, radiation fields are measured for each a plurality of arrangements of the applicator, which may for example be any of the applicators depicted in FIGS. 2a-2b, 3a-3b, 4a-4b, 5a-5b, 6, 7, and 8a-8b.

Different arrangements are achieved by inserting catheters are inserted into one, some, or all the openings or orifices of one or more graspers. More arrangements are achieved, by moving one or more catheters along the graspers, and setting each individual catheter at a plurality of distances from the target. If more than one catheter is present, further arrangements are achieved, by turning catheters on and off at different times according to predetermined timed patterns.

Optionally, more arrangements are achieved, by setting at least two graspers at a plurality of distances away from each other. In some variants, even more arrangements are achieved, by rotating graspers around at least one axis, for example by using a hinging mechanism, as shown in FIGS. 5a and 5b.

The mapping procedure is used for composing an atlas, in which of a plurality of predetermined radiation fields are matched to a plurality of arrangements, as described above.

At 1204, a radiation field is selected among the plurality of radiation fields included in the atlas. The radiation field is chose according to clinical needs, and at least one property of the target.

At 1204, the applicator is inserted in a closed configuration into a cavity, though an incision. As mentioned above, the applicator is compact in the closed configuration, and therefore easier to insert through a small sized incision. In an exemplary embodiment of the present invention, the size of the incision is 3-5 mm. The size of the incision may vary according to a clinical need.

At 1206, the applicator is switched to an open configuration, as described above.

At 1208, at least one catheter carrying a radiation generating material is inserted into the cavity. The catheter may be inserted into the cavity through the same incision used for inserting the applicator, or through a different incision, according to a user's preference.

At 1210, the catheter is grasped with a grasper of the applicator at a predetermined position along the catheter.

At 1212, the applicator is set at the arrangement corresponding to the desired radiation field.

At 1214, the selected radiation field is delivered to the target. Optionally, the radiation field is delivered by turning on and off on or more catheters according to a timed pattern, as described above.

The different manipulations of the applicator and/or of the catheter may be performed directly by a user, or through the help of manipulating tools controlled by the user, such as surgical robots.

Figure 14:
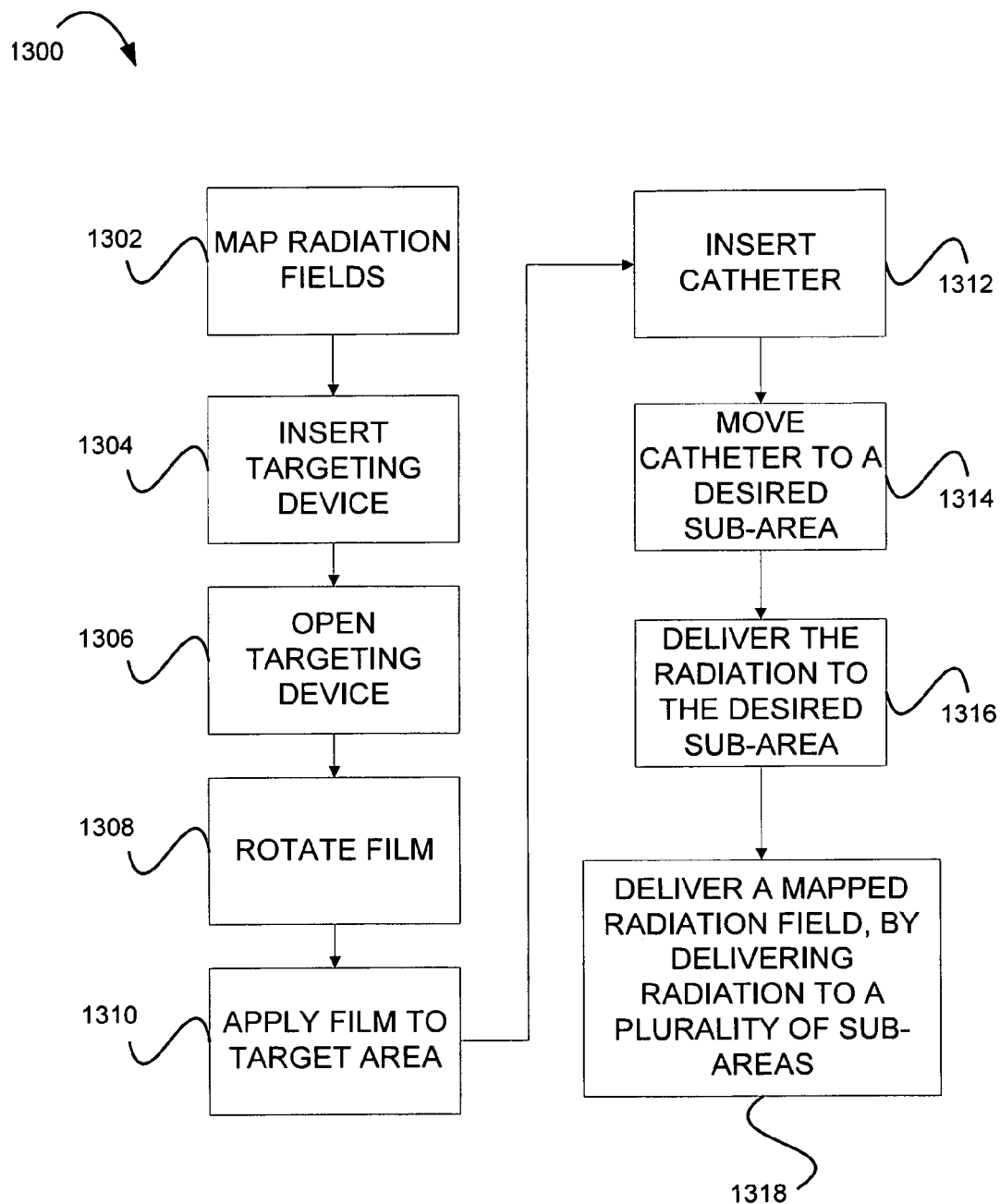
FIG. 14 is a flowchart illustrating a method for delivering radiation to a target area, according to some embodiments of the present invention.

FIG. 14 is a flowchart illustrating a method 1300 for delivering radiation to a target area, according to some embodiments of the present invention.

At 1302, a plurality of radiation fields is mapped. In the mapping, radiation fields are measured by measuring radiation applied for a selected amount of times over one or more sub-areas belonging to a surface.

At 1304, an aiming device, such as any of the devices of FIGS. 10a-10b, 11a-11b, and 12a-12b, is inserted in a closed configuration thereof into a cavity, though an incision. The aiming device is more compact in the closed configuration and is therefore easily inserted trough a small incision. An exemplary incision is 3-5 mm long. The size of the incision may vary according to a clinical need.

At 1306, the aiming device is switched to an open configuration of the device inside the cavity.

If needed, the film of the aiming device is rotated at 1308. According to some embodiments of the present invention, the rotation is performed about an axis which is not parallel to a central axis of the sheet, for example through a hinging mechanism, as described above. Optionally, the rotation takes place about an axis parallel to the central axis of the sheath, for example through a central rotating wire, as described above.

At 1310, the film is applied onto the target area, thereby dividing the target area into sub-areas defined by the grid. According to some embodiments of the present invention, the grid is composed of squares measuring about 5×5 mm. Grids of squares having different sizes may be used, according to a clinical need.

At 1312, a catheter carrying a radiation generating material is inserted into the cavity. The catheter may be inserted through the same incision through which the aiming device has been inserted, or through a different incision, according to a user's preference.

At 1314, the catheter is moved over a desired sub-area, at a predetermined distance away from the sub-area. Optionally, the distance from the sub-area is selected so that a uniform radiation is delivered to the sub-area. For example, if the sub-area is a square measuring about 5×5 mm, and the catheter includes an x-ray tube having a diameter of 5 mm, the distal end of the x-ray tube is placed about 5 mm away from the film, so that the radiation delivered to the sub-area is relatively uniform.

At 1316, radiation is delivered to the desired sub-area for a predetermined length of time, established during the mapping of 1302.

If needed, at 1318, the catheter is sequentially moved over a plurality of predetermined sub-areas, and radiation is delivered to each sub-area for a preset length of time. In this manner, the total radiation delivered to the target area is one of the plurality of mapped radiation fields.

The different manipulations of the applicator and/or of the catheter may be performed directly by a user, or through the help of manipulating tools controlled by the user, such as surgical robots.

While various embodiments of the present invention have been described above, it should be understood that they have been presented by way of example only, and not of limitation. Likewise, the various diagrams may depict an example architectural or other configuration for the invention, which is done to aid in understanding the features and functionality that can be included in the invention. The invention is not restricted to the illustrated example architectures or configurations, but the desired features can be implemented using a variety of alternative architectures and configurations. Indeed, it will be apparent to one of skill in the art how alternative functional, logical or physical partitioning and configurations can be implemented to implement the desired features of the present invention. Also, a multitude of different constituent module names other than those depicted herein can be applied to the various partitions. Additionally, with regard to flow diagrams, operational descriptions and method claims, the order in which the steps are presented herein shall not mandate that various embodiments be implemented to perform the recited functionality in the same order unless the context dictates otherwise.

Although the invention is described above in terms of various exemplary embodiments and implementations, it should be understood that the various features, aspects and functionality described in one or more of the individual embodiments are not limited in their applicability to the particular embodiment with which they are described, but instead can be applied, alone or in various combinations, to one or more of the other embodiments of the invention, whether or not such embodiments are described and whether or not such features are presented as being a part of a described embodiment. Thus the breadth and scope of the present invention should not be limited by any of the above-described exemplary embodiments.

Terms and phrases used in this document, and variations thereof, unless otherwise expressly stated, should be construed as open ended as opposed to limiting. As examples of the foregoing: the term "including" should be read as meaning "including, without limitation" or the like; the term "example" is used to provide exemplary instances of the item in discussion, not an exhaustive or limiting list thereof; the terms "a" or "an" should be read as meaning "at least one," "one or more" or the like; and adjectives such as "conventional," "traditional," "normal," "standard," "known" and terms of similar meaning should not be construed as limiting the item described to a given time period or to an item available as of a given time, but instead should be read to encompass conventional, traditional, normal, or standard technologies that may be available or known now or at any time in the future. Likewise, where this document refers to technologies that would be apparent or known to one of ordinary skill in the art, such technologies encompass those apparent or known to the skilled artisan now or at any time in the future.

A group of items linked with the conjunction "and" should not be read as requiring that each and every one of those items be present in the grouping, but rather should be read as "and/or" unless expressly stated otherwise. Similarly, a group of items linked with the conjunction "or" should not be read as requiring mutual exclusivity among that group, but rather should also be read as "and/or" unless expressly stated otherwise. Furthermore, although items, elements or components of the invention may be described or claimed in the singular, the plural is contemplated to be within the scope thereof unless limitation to the singular is explicitly stated.

The presence of broadening words and phrases such as "one or more," "at least," "but not limited to" or other like phrases in some instances shall not be read to mean that the narrower case is intended or required in instances where such broadening phrases may be absent. The use of the term "module" does not imply that the components or functionality described or claimed as part of the module are all configured in a common package. Indeed, any or all of the various components of a module, whether control logic or other components, can be combined in a single package or separately maintained and can further be distributed across multiple locations.

Additionally, the various embodiments set forth herein are described in terms of exemplary block diagrams, flow charts and other illustrations. As will become apparent to one of ordinary skill in the art after reading this document, the illustrated embodiments and their various alternatives can be implemented without confinement to the illustrated examples. For example, block diagrams and their accompanying description should not be construed as mandating a particular architecture or configuration.

What is claimed is:

1. An applicator for use in a minimally invasive surgical procedure and configured for manipulating one or more catheters carrying a radiation generating device, so as to deliver a radiation field to a target in a patient's body, the applicator having a proximal end and a distal end, the applicator comprising:
    a spring mechanism;
    at least one catheter grasper attached to the spring mechanism and configured for grasping the one or more catheters and for enabling insertion of the one or more catheters into the at least one catheter grasper and extraction of the one or more catheters from the at least one catheter grasper while the at least one catheter grasper is inside the patient's body; and
    a sheath, for covering at least a portion of the spring mechanism;
    wherein the spring mechanism is configured for being retracted within the sheath, in a closed configuration of the applicator;
    wherein the spring mechanism is configured for being released into a predetermined arrangement when moved out of a distal end of the sheath, in an open configuration of the applicator; and
    wherein the applicator is configured to be repeatedly switched between the closed configuration and the open configuration.

2. The applicator of claim 1, wherein the spring mechanism is configured for being attached to a plurality of catheter graspers.

3. The applicator of claim 1, for delivering one of a plurality of predetermined radiation fields to the target, wherein the at least one catheter grasper is configured for holding the one or more catheters at any of a plurality of predetermined positions along the one or more catheters, each position corresponding to one of the plurality of predetermined radiation fields.

4. The applicator of claim 1, for delivering one of a plurality of predetermined radiation fields to the target, wherein the spring mechanism is configured for assuming a plurality of predetermined arrangements in the open configuration, each arrangement corresponding to one of the plurality of the predetermined radiation fields.

5. The applicator of claim 1, wherein the spring mechanism comprises a plurality of wire springs, each wire spring being attached to at least one catheter grasper.

6. The applicator of claim 5, wherein proximal sections of the wire springs are joined together into a wire mesh, such that the wire springs are configured for being moved together along a direction of a central axis of the sheath.

7. The applicator of claim 6, wherein the wire mesh comprises a proximal wire mesh section and a distal wire mesh section, the sections being separated by a hinging mechanism, such that the hinging mechanism is configured for being controllably rotated, thereby rotating the distal wire mesh section together with the wire springs and the graspers, with respect to the proximal wire mesh section.

8. The applicator of claim 5, configured for holding a plurality of catheters, wherein the wire springs are configured to be released into the plurality of arrangements, each arrangement being characterized by a distance between at least two specific graspers, the distance between the graspers increasing as the wire springs are moved out of the distal end of the sheath, and decreasing, as the wire springs are retracted into the sheath.

9. The applicator of claim 5, further comprising an anchor, for keeping a distance between the wire springs fixed at an anchoring location along the wire springs, the anchor being attached to the wire springs and moving with the wire springs along the direction of the central axis of the sheath;
wherein the wire springs are fastened together at some locations proximal of the anchor, and are separated at locations distal of the anchor.

10. The applicator of claim 5, wherein the catheter graspers are set in line according to each other, so that each catheter grasper is configured to grasp a different section of a single catheter.

11. The applicator of claim 5, further comprising at least one straight wire for holding at least one further catheter grasper;
wherein the straight wire is configured for being moved with the plurality of wire springs, and does not form a curved shape when moved out of the distal end of the sheath.

12. The applicator of claim 1, wherein the at least one catheter grasper comprises one or more loops, each loop configured for receiving a respective catheter.

13. The applicator of claim 1, wherein the at least one catheter grasper comprises a panel having one or more orifices, each orifice configured for receiving a respective catheter.

* * * * *